(12) United States Patent
Baba-Ahmed et al.

(10) Patent No.: US 10,899,690 B2
(45) Date of Patent: Jan. 26, 2021

(54) METHOD FOR PURIFYING 1,1,1,2,2-PENTAFLUOROPROPANE AND METHOD FOR PREPARING 2,3,3,3-TETRAFLUORO-1-PROPENE

(71) Applicant: Arkema France, Colombes (FR)

(72) Inventors: Abdelatif Baba-Ahmed, Saint-fons (FR); Bertrand Collier, Saint-genis-laval (FR); Dominique Deur-Bert, Charly (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 210 days.

(21) Appl. No.: 16/063,775

(22) PCT Filed: Dec. 14, 2016

(86) PCT No.: PCT/EP2016/080943
§ 371 (c)(1),
(2) Date: Jun. 19, 2018

(87) PCT Pub. No.: WO2017/108517
PCT Pub. Date: Jun. 29, 2017

(65) Prior Publication Data
US 2020/0165181 A1    May 28, 2020

(30) Foreign Application Priority Data
Dec. 23, 2015 (FR) .................................... 15 63163

(51) Int. Cl.
C07C 17/386 (2006.01)
C07C 17/38 (2006.01)
(Continued)

(52) U.S. Cl.
CPC ............ *C07C 21/18* (2013.01); *C07C 17/383* (2013.01); *C07C 17/386* (2013.01); *C07C 19/08* (2013.01);
(Continued)

(58) Field of Classification Search
None
See application file for complete search history.

(56) References Cited

U.S. PATENT DOCUMENTS 5,470,422 A    11/1995 Mahler et al.
7,371,309 B2   5/2008 Boehmer et al.
(Continued)

FOREIGN PATENT DOCUMENTS

EP    0921109 A1   6/1999
EP    0939071 A1   9/1999
(Continued)

OTHER PUBLICATIONS

EPO, International Search Report in International Patent Application No. PCT/EP2016/080943 dated Mar. 8, 2017.

*Primary Examiner* — Medhanit W Bahta
(74) *Attorney, Agent, or Firm* — NK Patent Law

(57) ABSTRACT

The invention relates to a method for purifying 1,1,1,2,2-pentafluoropropane (245cb) using a first composition comprising 1,1,1,2,2-pentafluoropropane and at least one of the compounds selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-10 pentafluoropropene (1225ye-Z) and 3,3,3-trifluoropropene (1243zf), said method comprising the steps of: a) bringing said first composition into contact with at least one organic extraction agent in order to form a second composition; b)
(Continued)

extractive distillation of said second composition in order to form i) a third composition comprising said organic extraction agent and said at least one of the compounds selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf); and ii) a stream comprising the 1,1,1,2,2-pentafluoropropane; and c) recovery and separation of said third composition. The invention also relates to a method for producing 1234yf including the method for purifying 1,1,2,2-pentafluoropropane.

11 Claims, 4 Drawing Sheets

(51) Int. Cl.
  *C07C 19/08* (2006.01)
  *C07C 21/18* (2006.01)
  *C07C 17/383* (2006.01)
  *C09K 5/04* (2006.01)
(52) U.S. Cl.
  CPC ........ *C09K 5/045* (2013.01); *C09K 2205/126* (2013.01)

(56) References Cited

U.S. PATENT DOCUMENTS

| | | | |
|---|---|---|---|
| 2014/0191154 A1* | 7/2014 | Minor | C09K 3/30 252/68 |
| 2016/0031773 A1 | 2/2016 | Bonnet et al. | |
| 2017/0320798 A1* | 11/2017 | Shimokawa | C07C 17/386 |

FOREIGN PATENT DOCUMENTS

| | | |
|---|---|---|
| EP | 0743934 B1 | 11/1999 |
| EP | 0864554 B1 | 9/2002 |
| JP | 09508627 A | 9/1997 |
| JP | 2004505936 A | 2/2004 |
| JP | 2012524026 A | 10/2012 |
| JP | 2013521275 A | 6/2013 |
| WO | 9521148 A1 | 8/1995 |
| WO | 1998019982 A1 | 5/1998 |
| WO | 0212153 A1 | 2/2002 |
| WO | 2003068716 A1 | 8/2003 |
| WO | 2007079431 A2 | 7/2007 |
| WO | 2008040969 A2 | 4/2008 |
| WO | 2008054781 A1 | 5/2008 |
| WO | 2010123154 A2 | 10/2010 |
| WO | 2012011609 A1 | 1/2012 |
| WO | 2014147313 A1 | 9/2014 |
| WO | 2016080283 A1 | 5/2016 |

\* cited by examiner

METHOD FOR PURIFYING 1,1,1,2,2-PENTAFLUOROPROPANE AND METHOD FOR PREPARING 2,3,3,3-TETRAFLUORO-1-PROPENE

CROSS REFERENCE TO RELATED APPLICATIONS

This application is a U.S. National Stage application of International Application No. PCT/EP2016/080943 filed on Dec. 14, 2016, which claims the benefit of French Patent Application No. 1563163 filed on Dec. 23, 2015, the entire content of all of which is incorporated by reference herein.

TECHNICAL FIELD OF THE INVENTION

The invention relates to a process for preparing 2,3,3,3-tetrafluoro-1-propene. More particularly, the invention relates to a process for preparing 2,3,3,3-tetrafluoro-1-propene including the purification and recycling of 1,1,1,2,2-pentafluoropropane also derived from the reaction.

TECHNOLOGICAL BACKGROUND OF THE INVENTION

Hydrofluorocarbons (HFCs) and in particular hydrofluoroolefins (HFOs), such as 2,3,3,3-tetrafluoro-1-propene (HFO-1234yf), are compounds known for their properties as coolants, heat-transfer fluids, extinguishers, propellants, foaming agents, swelling agents, gaseous dielectrics, polymerization medium or monomer, support fluids, agents for abrasives, drying agents and fluids for power production units. HFOs have been identified as desirable alternatives to HCFC on account of their low ODP (ozone depletion potential) and GWP (global warming potential) values.

Most of the processes for manufacturing hydrofluoroolefins involve a fluorination and/or dehydrohalogenation reaction and/or a fluorination reaction. This type of reaction is performed in the gas phase and generates impurities which consequently need to be removed in order to obtain the desired compound in a sufficient degree of purity for the targeted applications.

For example, in the context of producing 2,3,3,3-tetrafluoro-1-propene (HFO-1234yf), the presence of impurities such as 1-chloro-3,3,3-trifluoro-1-propene (1233zd), 1,3,3,3-tetrafluoro-1-propene (1234ze) and 1,1,1,3,3-pentafluoropropane (245fa) is observed. These impurities are isomers of the main compounds that are desired to be obtained via the process for producing 2,3,3,3-tetrafluoro-1-propene, besides the latter, i.e. 2-chloro-3,3,3-trifluoro-1-propene (1233xf) and 1,1,1,2,2-pentafluoropropane (245cb). Given the respective boiling points of 1-chloro-3,3,3-trifluoro-1-propene (1233zd), 1,3,3,3-tetrafluoro-1-propene (1234ze) and 1,1,1,3,3-pentafluoropropane (245fa), they may accumulate in the reactor and thus prevent the formation of the products of interest.

Purification of this type of reaction mixture may be performed via various techniques known from the prior art, for instance distillation. However, when the compounds to be purified have boiling points that are too close or when they form azeotropic or quasi-azeotropic compositions, distillation is not an efficient process. Extractive distillation processes have thus been described.

EP 0 864 554 discloses a process for purifying a mixture comprising 1,1,1,3,3-pentafluoropropane (245fa) and 1-chloro-3,3,3-trifluoro-trans-1-propene (1233zd) by distillation in the presence of a solvent with a boiling point of greater than that of 1-chloro-3,3,3-trifluoro-trans-1-propene.

WO 03/068716 discloses a process for recovering pentafluoroethane from a mixture comprising pentafluoroethane and chloropentafluoroethane by distillation in the presence of hexafluoropropene.

WO 98/19982 also discloses a process for purifying 1,1-difluoroethane by extractive distillation. The process consists in placing an extracting agent in contact with a mixture of 1,1-difluoroethane and vinyl chloride. The extracting agent is chosen from hydrocarbons, alcohols and chlorocarbons with a boiling point of between 10° C. and 120° C. WO 2010/123154 describes a process for purifying 1,1,1,2,2-pentafluoropropane by distillation.

As mentioned by WO 98/19982, the selection of the extracting agent may prove to be complex depending on the products to be separated. There is thus still a need to develop a particular process for purifying 1,1,1,2,2-pentafluoropropane.

SUMMARY OF THE INVENTION

In a process for producing 2,3,3,3-tetrafluoro-1-propene, the choice of particular operating conditions makes it possible to promote the presence of certain impurities or isomers. 2,3,3,3-Tetrafluoro-1-propene may also be in equilibrium with 1,1,1,2,2-pentafluoropropane (245cb). Isolating and purifying the 1,1,1,2,2-pentafluoropropane (245cb) obtained is thus of particular interest for promoting the production of 2,3,3,3-tetrafluoro-1-propene (1234yf). In addition, the presence of impurities such as 1,3,3,3-tetrafluoro-1-propene (1234ze) may be observed, as may that of 1-chloro-3,3,3-trifluoro-1-propene (1233zd) and 1,1,1,3,3-pentafluoropropane (245fa). These impurities may derive from side reactions induced by intermediate compounds produced during the production of 2,3,3,3-tetrafluoro-1-propene, and may have physical properties such that the separation thereof with 1,1,1,2,2-pentafluoropropane (245cb) may prove to be complex. The present invention allows, besides the production of 2,3,3,3-tetrafluoro-1-propene, the recovery and recycling of the 1,1,1,2,2-pentafluoropropane (245cb) produced in excellent purity. Optionally, the 1,1,1,2,2-pentafluoropropane (245cb) thus recovered may undergo a dehydrofluorination reaction in the absence or presence of hydrofluoric acid to form 2,3,3,3-tetrafluoropropene. The 1,1,1,2,2-pentafluoropropane (245cb) thus recovered may undergo a fluorination reaction as described below.

According to a first aspect, the present invention provides a process for purifying 1,1,1,2,2-pentafluoropropane (245cb) from a first composition comprising 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf), said process comprising the steps of:

a) placing said first composition in contact with at least one organic extracting agent to form a second composition;

b) extractive distillation of said second composition to form and separate:

i) a third composition comprising said organic extracting agent and at least one compound chosen from the group consisting of 1,1-difluoroethane (152a), 1,1,1,2-tetrafluoroethane (134a), trans-1,3,3,3-tetrafluoro- 1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf); and ii) a stream comprising 1,1,1,2,2-pentafluoropropane;

c) recovery and separation of said third composition to form a stream comprising said organic extracting agent and a stream comprising said at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf); preferably, the organic extracting agent separated out in step c) is recycled into step a).

Preferably, the stream comprising the 1,1,1,2,2-pentafluoropropane formed in step a b) is recovered.

Preferably, the stream comprising said at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) separated out in step c) may be separated out to recover trans-1,3,3,3-tetrafluoro-1-propene (1234ze-E) when said stream contains same. Alternatively, said stream may be incinerated.

According to a preferred embodiment, said organic extracting agent is a solvent chosen from the group consisting of halohydrocarbon, alcohol, ketone, amine, ester, ether, aldehyde, nitrile, carbonate, thioalkyl, amide and heterocycle. Advantageously, said organic extracting agent is a solvent chosen from the group consisting of alcohol, ketone, amine, ester and heterocycle.

According to a preferred embodiment, said organic extracting agent has a boiling point of between 10 and 150° C.

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of 1,1,1,2,2-pentafluoropropane in said organic extracting agent at infinite dilution, P1 represents the saturating vapor pressure of 1,1,1,2,2-pentafluoropropane;

$\gamma_{2,S}$ represents the activity coefficient of said at least one compound consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) in said organic extracting agent at infinite dilution;

P2 represents the saturating vapor pressure of said at least one compound consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf); advantageously, the separation factor $S_{1,2}$ may be greater than or equal to 1.2, preferably greater than or equal to 1.4, more preferentially greater than or equal to 1.5, in particular greater than or equal to 1.8 and more particularly greater than or equal to 1.9.

In the present patent application, the saturating vapor pressure is considered for a temperature of 25° C.

According to a preferred embodiment, said organic extracting agent has an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of said at least one compound consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) in said organic extracting agent at infinite dilution; advantageously, the absorption capacity $C_{2,S}$ is greater than or equal to 0.40, preferably greater than or equal to 0.60, more preferentially greater than or equal to 0.80, in particular greater than or equal to 0.90, more particularly greater than or equal to 1.0 and preferentially greater than or equal to 1.05.

According to a preferred embodiment, said first composition is an azeotropic or quasi-azeotropic composition comprising 1,1,1,2,2-pentafluoropropane (245cb) and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

Preferably, the first composition is an azeotropic or quasi-azeotropic composition comprising 1,1,1,2,2-pentafluoropropane (245cb) and trans-1,3,3,3-tetrafluoro-1-propene (1234ze-E). Said organic extracting agent has a separation factor $S_{1,2}$ of greater than or equal to 1.5, said separation factor being calculated by the formula $S_{1,2}=(\gamma_{1,S}*P1)/(\gamma_{2,S}*P2)$ in which $\gamma_{1,S}$ represents the activity coefficient of 1,1,1,2,2-pentafluoropropane in said organic extracting agent at infinite dilution;

P1 represents the saturating vapor pressure of 1,1,1,2,2-pentafluoropropane;

$\gamma_{2,S}$ represents the activity coefficient of trans-1,3,3,3-tetrafluoro-1-propene in said organic extracting agent at infinite dilution;

P2 represents the saturating vapor pressure of trans-1,3,3,3-tetrafluoro-1-propene.

Preferably, said organic extracting agent has an absorption capacity $C_{2,S}$ of greater than or equal to 0.60, said absorption capacity being calculated by the formula $C_{2,S}=1/(\gamma_{2,S})$ in which $\gamma_{2,S}$ represents the activity coefficient of trans-1,3,3,3-tetrafluoro-1-propene in said organic extracting agent at infinite dilution. In particular, said organic extracting agent is chosen from the group consisting of ethylamine, isopropylamine, n-propylamine, diethylamine, propanone, tetrahydrofuran, ethyl acetate, butanone, 3-pentylamine, 2-methoxyethanamine, dioxane, 3-pentanone, 2-pentanone, n-pentylamine, 1,3-dioxane, 1,2-diaminoethane, 1,2-propanediamine, 2-methoxyethanol, n-butyl acetate and 1-ethoxy-2-propanol. More particularly, said organic extracting agent is chosen from the group consisting of ethylamine, isopropylamine, n-propylamine, diethylamine, tetrahydrofuran, ethyl acetate, butanone, 3-pentylamine, 2-methoxyethanamine, dioxane, 2-pentanone, n-pentylamine, 1,3-dioxane, 1,2-diaminoethane, 1,2-propanediamine, 2-methoxyethanol, n-butyl acetate and 1-ethoxy-2-propanol.

According to a preferred embodiment, the 1,1,1,2,2-pentafluoropropane separated out in step b) is recovered to be used in a process for producing 2,3,3,3-tetrafluoro-1-propene.

According to a preferred embodiment, said first composition used in step a) is obtained from a composition comprising 2,3,3,3-tetrafluoro-1-propene (1234yf).

According to a preferred embodiment, the process comprises, prior to step a), the following steps:
i') implementation of a composition A comprising 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf), and, optionally or not, impurities with a boiling point below the boiling point of 2,3,3,3-tetrafluoro-1-propene;
ii') optionally or not, distillation of said composition of 2,3,3,3-tetrafluoro-1-propene to remove, at the top of the column, impurities with a boiling point below the boiling point of 2,3,3,3-tetrafluoro-1-propene and to form a first stream comprising 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) recovered at the bottom of the distillation column;
iii') distillation of said first stream recovered at the bottom of the distillation column in step ii') or of composition A to form and recover, at the top of the distillation column, a second stream comprising 2,3,3,3-tetrafluoro-1-propene and to form and recover, at the bottom of the distillation column, a third stream comprising 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) corresponding to said first composition used in step a) of the process for purifying 1,1,1,2,2-pentafluoropropane according to the present invention.

According to a particular embodiment, said third stream formed and recovered in step iii') may contain 2,3,3,3-tetrafluoro-1-propene derived from composition A or from said first stream obtained in ii'), advantageously in low proportion expressed as a weight percentage relative to the total weight of said third stream, preferably in a proportion less than that of the 1,1,1,2,2-pentafluoropropane expressed as a weight percentage relative to the total weight of said third stream. Advantageously, said third stream formed and recovered in step iii') may contain less than 10% by weight, advantageously less than 5% by weight and preferably less than 1% by weight of 2,3,3,3-tetrafluoro-1-propene relative to the total weight of said third stream. In this case, during the implementation of steps a) and b) of the present purification process, 2,3,3,3-tetrafluoro-1-propene will be recovered in the stream formed and recovered in step b) comprising 1,1,1,2,2-pentafluoropropane.

According to a second aspect of the present invention, a process for producing 2,3,3,3-tetrafluoro-1-propene is provided. Said process comprises the steps of:
A) fluorination, in the presence of a catalyst, of a compound of formula $CX(Y)_2$—$CX(Y)_m$—$CH_mXY$ (I) in which X and Y independently represent H, F or Cl and m=0 or 1;
and/or fluorination, in the presence of a catalyst, of a compound of formula $(CX_nY_{3-n})\,CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;
B) recovery of a stream comprising 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf);
C) distillation of the stream recovered in step B) and recovery, at the top of the distillation column, of a stream comprising 2,3,3,3-tetrafluoro-1-propene, and, at the bottom of the distillation column, a stream comprising 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf);
C) implementation of the process for purifying 1,1,1,2,2-pentafluoropropane according to the present invention using the stream recovered at the bottom of the distillation column in step C); and
E) recycling into step A) of the stream comprising 1,1,1,2,2-pentafluoropropane formed in step b) of the process for purifying 1,1,1,2,2-pentafluoropropane performed in step D) or dehydrofluorination of the stream comprising 1,1,1,2,2-pentafluoropropane formed in step b) of the process for purifying 1,1,1,2,2-pentafluoropropane performed in step D) in the absence or presence of hydrofluoric acid.

According to another aspect, the invention provides a composition comprising 1,1,1,2,2-pentafluoropropane, trans-1,3,3,3-tetrafluoro-1-propene and an organic extracting agent with a separation factor $S_{1,2}$ of greater than or equal to 1.5, said separation factor being calculated by the formula $S_{1,2}=(\gamma_{1,S}*P1)/(\gamma_{2,S}*P2)$ in which $\gamma_{1,S}$ represents the activity coefficient of 1,1,1,2,2-pentafluoropropane in said organic extracting agent at infinite dilution, P1 represents the saturating vapor pressure of 1,1,1,2,2-pentafluoropropane, $\gamma_{2,S}$ represents the activity coefficient of trans-1,3,3,3-tetrafluoro-1-propene in said organic extracting agent at infinite dilution and P2 represents the saturating vapor pressure of trans-1,3,3,3-tetrafluoro-1-propene. Advantageously, said organic extracting agent has an absorption capacity $C_{2,S}$ of greater than or equal to 0.60, said absorption capacity being calculated by the formula $C_{2,S}=1/(\gamma_{2,S})$ in which $\gamma_{2,S}$ represents the activity coefficient of trans-1,3,3,3-tetrafluoro-1-propene in said organic extracting agent at infinite dilution.

Preferably, the organic extracting agent is chosen from the group consisting of ethylamine, isopropylamine, n-propylamine, diethylamine, propanone, tetrahydrofuran, ethyl acetate, butanone, 3-pentylamine, 2-methoxyethanamine, dioxane, 3-pentanone, 2-pentanone, n-pentylamine, 1,3-dioxane, 1,2-diaminoethane, 1,2-propanediamine, 2-methoxyethanol, n-butyl acetate and 1-ethoxy-2-propanol. In particular, the organic extracting agent is chosen from the group consisting of ethylamine, isopropylamine, n-propylamine, diethylamine, propanone, tetrahydrofuran, ethyl acetate, butanone, 3-pentylamine, 2-methoxyethanamine, dioxane, 3-pentanone, 2-pentanone, n-pentylamine, 1,3-dioxane, 1,2-diaminoethane, 1,2-propanediamine, 2-methoxyethanol, n-butyl acetate and 1-ethoxy-2-propanol.

According to another aspect, the invention provides an azeotropic or quasi-azeotropic composition comprising 50% to 99.99% by weight of 1,1,1,2,2-pentafluoropropane relative to the total weight of the composition and 0.01% to 50% by weight of trans-1,3,3,3-tetrafluoro-1-propene relative to the total weight of the composition.

According to another aspect, the invention also provides an azeotropic or quasi-azeotropic composition comprising 50% to 99.99% by weight of 1,1,1,2,2-pentafluoropropane relative to the total weight of the composition, and 0.01% to 50% by weight of at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) relative to the total weight of the composition.

According to another aspect, the invention provides an azeotropic or quasi-azeotropic composition comprising 50% to 99.99% by weight of 1,1,1,2,2-pentafluoropropane, less than 50% by weight of trans-1,3,3,3-tetrafluoro-1-propene relative to the total weight of the composition, and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

DETAILED DESCRIPTION OF THE INVENTION

Figure 1A:
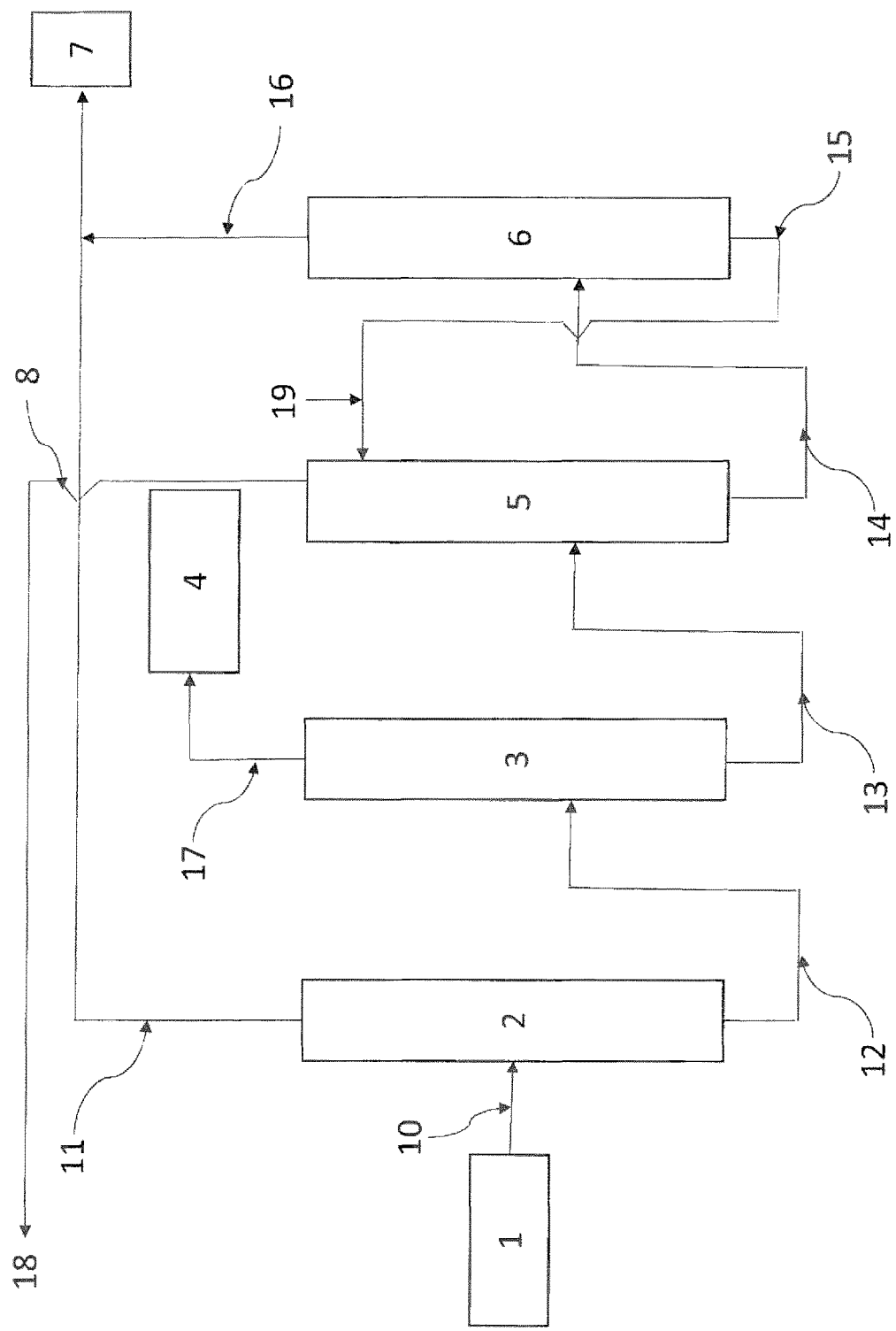
FIGS. 1a-c schematically represent a device for performing a process for purifying 1,1,1,2,2-pentafluoropropane according to a particular embodiment of the present invention.

The term "hydrocarbon" as used herein refers to linear or branched $C_1$-$C_{20}$ alkane, $C_3$-$C_{20}$ cycloalkane, $C_5$-$C_{20}$ alkene, $C_5$-$C_{20}$ cycloalkene or $C_6$-$C_{18}$ arene compounds. For example, the term "alkane" refers to compounds of formula $C_nH_{2n+2}$ in which n is between 1 and 20. The term "$C_1$-$C_{20}$ alkane" includes, for example, pentane, hexane, heptane, octane, nonane and decane, or isomers thereof. The term "$C_5$-$C_{20}$ alkene" refers to hydrocarbon-based compounds comprising one or more carbon-carbon double bonds and comprising from 5 to 20 carbon atoms. The term "$C_3$-$C_{20}$ cycloalkane" refers to a saturated hydrocarbon-based ring comprising from 3 to 20 carbon atoms. The term "$C_6$-$C_{18}$ aryl" refers to cyclic and aromatic hydrocarbon-based compounds comprising from 6 to 18 carbon atoms. The term "$C_5$-$C_{20}$ cycloalkene" refers to cyclic hydrocarbon-based compounds comprising from 5 to 20 carbon atoms and comprising one or more carbon-carbon double bonds.

The term "alkyl" denotes a monovalent radical derived from a linear or branched alkane, comprising from 1 to 20 carbon atoms. The term "cycloalkyl" denotes a monovalent radical derived from a cycloalkane, comprising from 3 to 20 carbon atoms. The term "aryl" denotes a monovalent radical derived from an arene, comprising from 6 to 18 carbon atoms. The term "alkenyl" denotes a monovalent radical of 2 to 20 carbon atoms and at least one carbon-carbon double bond. The term "alkynyl" denotes a monovalent radical of 2 to 20 carbon atoms and at least one carbon-carbon triple bond. The term "halogen" refers to an —F, —Cl, —Br or —I group. The term "cycloalkenyl" refers to a monovalent radical derived from a cycloalkene comprising from 3 to 20 carbon atoms. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl substituents may be optionally substituted with one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H or —C(O)R$^a$ substituents in which R$^a$ and R$^b$ are, independently of each other, hydrogen, unsubstituted $C_1$-$C_{20}$ alkyl, unsubstituted $C_2$-$C_{20}$ alkenyl, unsubstituted $C_2$-$C_{20}$ alkynyl, unsubstituted $C_3$-$C_{20}$ cycloalkyl, unsubstituted $C_3$-$C_{20}$ cycloalkenyl or unsubstituted $C_6$-$C_{18}$ aryl. In the substituents —NR$^a$R$^b$, R$^a$ and R$^b$ may form, with the nitrogen atom to which they are attached, a saturated or unsaturated, aromatic or non-aromatic, 5- to 10-membered heterocycle.

The term "halohydrocarbons" refers to compounds of formula R$^a$X in which R$^a$ is chosen from $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl and X represents a chlorine, fluorine, bromine or iodine atom. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl substituents may be optionally substituted with one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H or —C(O)R$^a$ substituents in which R$^a$ and R$^b$ are as defined above.

The term "alcohol" refers to hydrocarbons or halohydrocarbons as defined above in which at least one hydrogen atom is replaced with a hydroxyl group —OH.

The term "ketone" refers to hydrocarbons comprising at least one or more carbonyl functional groups R$^c$—C(O)—R$^d$ in which R$^c$ and R$^d$ are, independently of each other, a $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl or $C_6$-$C_{18}$ aryl and may be optionally substituted with one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H or —C(O)R$^a$ substituents in which R$^a$ and R$^b$ are as defined above, R$^c$ and R$^d$ possibly being linked together to form, with the carbonyl group to which they are attached, a 4- to 10-membered and preferably 4- to 7-membered cyclic ketone. The cyclic ketone may also comprise one or more carbon-carbon double bonds. The cyclic ketone may also be optionally substituted with one or more substituents as defined above.

The term "amine" refers to hydrocarbons comprising at least one or more amine functional groups —NR$^c$R$^d$ in which R$^c$ and R$^d$ are as defined above, R$^c$ and R$^d$ possibly being linked together to form, with the nitrogen atom to which they are attached, a 4- to 10-membered aromatic or non-aromatic heterocycle.

The term "esters" refers to compounds of formula R$^c$—C(O)—O—R$^d$ in which R$^c$ and R$^d$ are as defined above, R$^c$ and $R^d$ possibly being linked together to form, with the ester group, a ring comprising from 4 to 20 carbon atoms.

The term "ether" refers to compounds of formula $R^c$—O—$R^d$ in which $R^c$ and $R^d$ are as defined above, $R^c$ and $R^d$ possibly being linked together to form, with the oxygen atom to which they are attached, a heterocycle comprising from 4 to 20 carbon atoms.

The term "aldehyde" refers to compounds comprising at least one or more —C(O)—H functional groups.

The term "nitrile" refers to compounds comprising at least one or more —CN functional groups.

The term "carbonate" refers to compounds of formula $R^c$—O—C(O)—O—$R^d$ in which $R^c$ and $R^d$ are as defined above.

The term "thioalkyl" refers to compounds of formula $R^cSR^d$ in which $R^c$ and $R^d$ are as defined above.

The term "amide" relates to compounds of formula $R^cC(O)NR^eR^d$ in which $R^c$ and $R^d$ are as defined above, $R^e$ having the same definition as $R^c$, $R^c$ and $R^d$ possibly being linked together to form, with the amide group —C(O)N— to which they are attached, a 4- to 10-membered and preferably 4- to 7-membered cyclic amide. The cyclic amide may also comprise one or more carbon-carbon double bonds. The cyclic amide may also be optionally substituted with one or more substituents as defined above.

The term "heterocycle" denotes a 4- to 10-membered carbon-based ring, at least one of the ring members of which is a heteroatom chosen from the group consisting of O, S, P and N. The ring may comprise one or more carbon-carbon double bonds or one or more carbon-heteroatom double bonds or one or more heteroatoms-heteroatom double bonds. Preferably, the heterocycle may comprise 1, 2, 3, 4 or 5 heteroatoms as defined above. In particular, the heterocycle may comprise 1, 2 or 3 heteroatoms chosen from oxygen, nitrogen and sulfur. Preferably, the heterocycle may be a 4- to 6-membered carbon-based ring, 1, 2 or 3 ring members of which are heteroatoms chosen from 0 and N. The heterocycle may be optionally substituted with one or more substituents chosen from —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H and —C(O)R$^a$ in which R$^a$ and R$^b$ are as defined above.

The term "azeotropic composition" denotes a liquid mixture of two or more compounds which behave like a single substance, and which boils at a fixed temperature maintaining a composition in the liquid phase identical to that in the gas phase. The term "quasi-azeotropic composition" denotes a liquid mixture of two or more compounds having a constant boiling point or which has a tendency not to fractionate when it is subjected to boiling or to evaporation.

The term "organic extracting agent" refers to a compound comprising at least one carbon atom.

According to a first aspect, the invention relates to a process for purifying 1,1,1,2,2-pentafluoropropane (245cb). The purification process is performed using a first composition comprising 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

Preferably, said process comprises the steps of:
a) placing said first composition in contact with at least one organic extracting agent to form a second composition;
b) extractive distillation of said second composition to form:
  i) a third composition comprising said organic extracting agent and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf); and
  ii) a stream comprising 1,1,1,2,2-pentafluoropropane;
c) recovery and separation of said third composition to form a stream comprising said organic extracting agent and a stream comprising said at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

The extracting agent separated out in step c) may be recovered and recycled into step a).

Alternatively, step c) may be optional.

Said first composition may comprise 1,1,1,2,2-pentafluoropropane and at least two, at least three, at least four, at least five, at least six or all of the compounds chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

Said first composition may comprise between 50% and 99.99% by weight of 1,1,1,2,2-pentafluoropropane relative to the total weight of the first composition, advantageously between 60% and 99.9% by weight, preferably between 70% and 99.8% and in particular between 75% and 99.5% by weight of 1,1,1,2,2-pentafluoropropane relative to the total weight of the first composition.

When it contains same, said first composition may comprise less than 2000 ppm by weight of 1,1-difluoroethane (152a) relative to the total weight of the first composition, advantageously between 1 and 1000 ppm by weight, preferably between 5 and 500 ppm and in particular between 10 and 250 ppm by weight of 1,1-difluoroethane (152a) relative to the total weight of the first composition.

When it contains same, said first composition may comprise less than 2000 ppm by weight of 1,1,1,2-tetrafluoroethane (134a) relative to the total weight of the first composition, advantageously between 1 and 1000 ppm by weight, preferably between 5 and 500 ppm and in particular between 10 and 250 ppm by weight of 1,1,1,2-tetrafluoroethane (134a) relative to the total weight of the first composition.

When it contains same, said first composition may comprise less than 50% by weight of trans-1,3,3,3-tetrafluoro-1-propene (1234ze-E) relative to the total weight of the first composition, advantageously between 0.1% and 40% by weight, preferably between 0.2% and 30% and in particular between 0.5% and 25% by weight of trans-1,3,3,3-tetrafluoro-1-propene (1234ze-E) relative to the total weight of the first composition.

When it contains same, said first composition may comprise less than 5000 ppm by weight of cis-1,3,3,3-tetrafluoro-1-propene (1234ze-Z) relative to the total weight of the first composition, advantageously between 1 and 2000 ppm by weight, preferably between 5 and 1000 ppm and in particular between 10 and 500 ppm by weight of cis-1,3,3,3-tetrafluoro-1-propene (1234ze-Z) relative to the total weight of the first composition.

When it contains same, said first composition may comprise less than 2000 ppm by weight of trans-1,2,3,3,3-pentafluoropropene (1225ye-E) relative to the total weight of the first composition, advantageously between 1 and 1000 ppm by weight, preferably between 5 and 500 ppm and in particular between 10 and 250 ppm by weight of trans-1,2,3,3,3-pentafluoropropene (1225ye-E) relative to the total weight of the first composition.

When it contains same, said first composition may comprise less than 2000 ppm by weight of cis-1,2,3,3,3-pentafluoropropene (1225ye-Z) relative to the total weight of the first composition, advantageously between 1 and 1000 ppm by weight, preferably between 5 and 500 ppm and in particular between 10 and 250 ppm by weight of cis-1,2,3,3,3-pentafluoropropene (1225ye-Z) relative to the total weight of the first composition.

When it contains same, said first composition may comprise less than 1% by weight of 3,3,3-trifluoropropene (1243zf) relative to the total weight of the first composition, advantageously between 1 and 5000 ppm by weight, preferably between 5 and 2000 ppm and in particular between 10 and 1500 ppm by weight of 3,3,3-trifluoropropene (1243zf) relative to the total weight of the first composition.

According to a particular embodiment, said organic extracting agent is a solvent chosen from the group consisting of halohydrocarbon, alcohol, ketone, amine, ester, ether, aldehyde, nitrile, carbonate, thioalkyl, amide and heterocycle. In particular, said organic extracting agent is a solvent chosen from the group consisting of alcohol, ketone, amine, ester and heterocycle. Preferably, the heterocycle is a 4- to 6-membered heterocycle, 1, 2 or 3 ring members of which are heteroatoms such as O or N.

Preferably, the halohydrocarbons are chosen from the group consisting of iodomethane, bromoethane, chlorobromomethane, iodoethane, 2-bromopropane, dichlorobromomethane, 2-chloropropane, 2-iodopropane, bromotrichloromethane, trichloroacetaldehyde, 1,2-dibromopropane, 2-bromobutane, 1,2-dichloropropane, 1,1,2-trichloroethane, 1,2,3-trichloropropene, 1,2-dibromoethane, 1-bromopropane, 3-bromopropene, 1-bromo-2-chloroethane, 1,2-dichloroethane, 1-iodopropane, 2-bromopentane, 1-bromo-3-methylbutane, tribromomethane, 1-bromobutane, 1-chloro-3-bromopropane, 1-bromopentane, 1,3-dichloropropane, 1-bromo-3-fluoropropane, 1,2-dibromo-1-fluoroethane, 1-bromo-1,2-difluoroethylene, bromofluoromethane, 1,1,1-trifluoro-2-bromoethane, 1-chloro-3-fluoropropane, 1-chloro-4-fluorobutane, 2-bromo-2-methylpropane, 2-chloro-2-methylpropane, 2-bromo-2-methylbutane, 2,3-dichloro-2-methylbutane, 1-iodobutane, 1,1,2-trichloropropane, 1,3-dichlorobutane, 2,3-dichlorobutane, 1,2,2-trichloropropane, cis-1,3-dichloropropene, trans-1,3-dichloropropene, 1,3-dichloro-trans-2-butene, 1,2-dichloro-2-butene and 2-chloro-2-methylbutane.

Preferably, the alcohols are chosen from the group consisting of methanol, ethanol, 2-propanol, 2,2-dimethyl-1-propanol, 2,2,2-trifluoroethanol, tert-butanol, 2,2,3,3-tetraflouro-1-propanol, 2-chloro-1-propanol, propanol, 2-allyloxyethanol, 2-butanol, 2-aminophenol, 2-methyl-2-butanol, 2-ethyl-1-butanol, isobutanol, 3-pentanol, 1-butanol, 1-methoxy-2-propanol, 1-(dimethylamino)-2-propanol, 2-methyl-1-pentanol, 3-methyl-3-pentanol, 2-methoxy-1-propanol, 1-ethoxy-2-propanol, 4-methyl-2-pentanol, 2-chloroethanol, 1,2-octanediol, 2-(dimethylamino)ethanol, 3-hexanol, 2-hexanol, 2-ethoxy-1-propanol, 1-pentanol, 2-propoxyethanol, 1-propoxy-2-propanol, 2,2-difluoroethanol, 1,1,1-trifluoro-2-propanol, 4,4,4-trifluorobutanol, 3-fluoropropanol, 2,3-dimethylbutanol and 1-chloro-2-methyl-2-propanol.

Preferably, the ketones are chosen from the group consisting of propanone, butanone, 3-pentanone, 2-pentanone, 3,3-dimethyl-2-butanone, 4-methyl-2-pentanone, 2-hexanone, 5-hexen-2-one, 4-methyl-2-hexanone, and 1,1,1-trifluoro-2-propanone.

Preferably, the amines are chosen from the group consisting of ethylamine, isopropylamine, ethylmethylamine, 2-amino-2-methylpropane, n-propylamine, isopropylmethylamine, diethylamine, 2-butanamine, n-methylpropylamine, 1-butylamine, diisopropylamine, 3-methyl-2-butanamine, 3-pentylamine, n-methylbutylamine, 1-methoxy-2-propanamine, 2-methoxyethanamine, 2-methoxy-1-propanamine, n-pentylamine, n-methylhydroxylamine, dipropylamine, 2-ethoxyethanamine, n-methyl-1,2-ethanediamine, pyridine, 1,2-diaminoethane, 1,2-propanediamine, 2-ethylbutylamine, n-ethylethylenediamine, 2-methylpyridine, 4-methyl-2-hexanamine, hexylamine, cyclohexylamine, n-ethyl-2-dimethylaminoethylamine, 1,3-propanediamine, 2-heptanamine, n,n-diethylethylenediamine, 2,6-dimethylpyridine, 4-methylpyridine, n,n'-diethyl-1,2-ethanediamine, dimethylethanolamine and 1,1-diethoxy-n,n-dimethylmethanamine.

Preferably, the esters are chosen from the group consisting of methyl acetate, ethyl acetate, n-propyl formate, isopropyl acetate, tert-butyl acetate, ethyl propionate, sec-butyl acetate, diethyl carbonate, n-butyl acetate, bromoacetic acid methyl ester, methyl formate, methyl hexanoate and isopropyl formate.

Preferably, the ethers are chosen from the group consisting of diethyl ether, 2-ethoxypropane, methyl t-butyl ether, 2,2-dimethoxypropane, 1-ethoxy-2-methylpropane, 1,2-dimethoxyethane, diethoxymethane, 1-ethoxybutane, 1-methoxypentane, 1,2-dimethoxypropane, 1,1-diethoxyethane, trimethoxymethane, 2-chloro-1,1-dimethoxyethane, 2,2-diethoxypropane, 1,1-diethoxypropane, 2-methoxyethanol, methoxycyclohexane, chloromethoxymethane, ethoxyethanol, di-n-butyl ether, diisopropyl ether, 1-ethoxyhexane, 1,1,1-triethoxyethane, 1-methoxy-2-acetoxypropane, dimethoxymethane, ethoxyethene, di-n-propyl ether, 2-methoxy-1-propene, 2,2,2-trifluoroethyl methyl ether, methyl cyclopropyl ether, 2-ethoxy-2-methylpropane, 2-ethoxybutane, sec-butyl tert-butyl ether, isobutyl tert-butyl ether, 1-methoxy-2-methylbutane and isopropyl isobutyl ether.

Preferably, the aldehydes are chosen from the group consisting of acetaldehyde, isobutanal, methylglyoxal, 2-methylbutanal, 2,6-dimethyl-5-heptenal, hexanal and ethanedial.

Preferably, the nitriles are chosen from the group consisting of acetonitrile, propionitrile, butyronitrile, valeronitrile and (methyleneamino)acetonitrile.

Preferably, the carbonate is diethyl carbonate.

Preferably, the amides include ethanethioamide.

Preferably, the thioalkyls are chosen from the group consisting of ethanethiol, dimethyl sulfide, 2-propanethiol, tert-butylthiol, 3-mercapto-1,2-propanediol, 1-propanethiol, butanethiol, tetrahydrothiophene, 1-pentanethiol, diethyl sulfide, 2-butanethiol, 2-methyl-1-propanethiol and 4-methoxy-2-methyl-2-butanethiol.

Preferably, the heterocycles are chosen from the group consisting of n-ethylmorpholine, 1-methylpiperazine, n-methylmorpholine, 2-methylpyrazine, tetrahydrofuran, 1,3,5-trioxane, dioxane, 1,3-dioxane, piperidine and 2,6-dimethylmorpholine. Dioxane refers to 1,4-dioxane.

Said organic extracting agent may be ethylamine, bromofluoromethane, 1-bromo-1,2-difluoroethylene, acetaldehyde, 1,1,1-trifluoro-2-propanone, 1,1,1-trifluoro-2-bromoethane, 2,2,2-trifluoroethyl methyl ether, isopropylamine, methyl formate, 2-methoxy-1-propene, diethyl ether, 1,2-epoxypropane, ethanethiol, ethoxyethene, ethylmethylamine, dimethyl sulfide, 2-chloropropane, bromoethane, dimethoxymethane, iodomethane, 2-amino-2-methylpropane, methyl cyclopropyl ether, n-propylamine, isopropylmethylamine, ethanedial, 2-chloro-2-methylpropane, 2-propanethiol, 2-ethoxypropane, methyl t-butyl ether, diethylamine, propanone, methyl acetate, 4-methoxy-2-methyl-2-butanethiol, 2-bromopropane, chloromethoxymethane, 2-butanamine, n-methylpropylamine, tert-butylthiol, isobutanal, methanol, tetrahydrofuran, 1-propanethiol, chlorobromomethane, isopropyl formate, diisopropyl ether, 3-bromopropene, 1-bromopropane, methylglyoxal, iodoethane, 2-ethoxy-2-methylpropane, 2-bromo-2-methylpropane, 2,2,2-trifluoroethanol, 1-chloro-3-fluoropropane, 1,1,1-trifluoro-2-propanol, 1-butylamine, ethyl acetate, ethanol, butanone, n-propyl formate, 2-ethoxybutane, 2-propanol, acetonitrile, tert-butanol, 1-methoxy-2-methylbutane, 2,2-dimethoxypropane, 2-chloro-2-methylbutane, 1,2-dichloroethane, 1-ethoxy-2-methylpropane, diisopropylamine, 2-butanethiol, 1,2-dimethoxyethane, 3-methyl-2-butanamine, diethoxymethane, 2-methyl-1-propanethiol, isopropyl acetate, 2-iodopropane, di-n-propyl ether, 3-pentylamine, n-methylbutylamine, 2-bromobutane, diethyl sulfide, 1-ethoxybutane, 1-methoxy-2-propanamine, 2-methylbutanal, 2-methoxyethanamine, 2,2-difluoroethanol, 1,2-dichloropropane, propanol, tert-butyl acetate, propionitrile, trichloroacetaldehyde, 2-allyloxyethanol, butanethiol, 1-methoxypentane, ethyl propionate, 2-butanol, 1,2-dimethoxypropane, isopropyl isobutyl ether, 1-chloro-4-fluorobutane, 1-bromo-3-fluoropropane, dioxane, 1-bromobutane, 3-pentanone, 1,1-diethoxyethane, 2-pentanone, 2-methyl-2-butanol, 1-iodopropane, 2-methoxy-1-propanamine, trimethoxymethane, cis-1,3-dichloropropene, n-pentylamine, 3,3-dimethyl-2-butanone, 1,3-dioxane, piperidine, 1-bromo-2-chloroethane, isobutanol, 2-bromo-2-methylbutane, dipropylamine, 2,2,3,3-tetraflouro-1-propanol, 2-ethoxyethanamine, triethylfluorosilane, sec-butyl acetate, trans-1,3-dichloropropene, 2,2-dimethyl-1-propanol, n-methyl-1,2-ethanediamine, 2,2-diethoxypropane, 1,3,5-trioxane, pyridine, n-methylmorpholine, 3-pentanol, 4-methyl-2-pentanone, 1,2-diaminoethane, isobutyl tert-butyl ether, 2-bromopentane, butyronitrile, 1-butanol, 2,3-dichlorobutane, sec-butyl tert-butyl ether, 1-methoxy-2-propanol, 1,2-propanediamine, 2,6-dimethyl-5-heptenal, 1-bromo-3-methylbutane, 1,3-dichloro-trans-2-butene, 1,3-dichloropropane, 1-(dimethylamino)-2-propanol, tetrahydrothiophene, 3-methyl-3-pentanol, 1,2-dibromo-1-fluoroethane, 1,1-diethoxypropane, 1,2,2-trichloropropane, 1-chloro-2-methyl-2-propanol, 2-methoxyethanol, 4,4,4-trifluorobutanol, 2-ethylbutylamine, diethyl carbonate, n-butyl acetate, 1-pentanethiol, 2-chloro-1,1-dimethoxyethane, 2-hexanone, n-ethylethylenediamine, 3-fluoropropanol, 5-hexen-2-one, 2,3-dichloro-2-methylbutane, 1,1-diethoxy-n,n-dimethylmethanamine, 2-methylpyridine, 1-bromopentane, 2-methoxy-1-propanol, 1,2-dichloro-2-butene, 1-iodobutane, hexanal, 1-ethoxy-2-propanol, 1,2-dibromoethane, 4-methyl-2-pentanol, bromoacetic acid methyl ester, 1,1,2-trichloropropane, 1,2-octanediol, 4-methyl-2-hexanamine, hexylamine, 2-chloro-1-propanol, methoxycyclohexane, 2-(dimethylamino)ethanol, 1,3-dichlorobutane, cyclohexylamine, n-ethyl-2-dimethylaminoethylamine, ethoxyethanol, 3-hexanol, 2-hexanol, 2-methylpyrazine, 2-ethoxy-1-propanol, 1-pentanol, n-ethylmorpholine, 1-methylpiperazine, 1,3-propanediamine, di-n-butyl ether, valeronitrile, (methyleneamino)acetonitrile, 1,2-dibromopropane, 1,2,3-trichloropropene, 2-heptanamine, 2,3-dimethylbutanol, 1-ethoxyhexane, 1-chloro-3-bromopropane, n,n-diethylethylenediamine, 3-furfural, 2,6-dimethylpyridine, 4-methyl-2-hexanone, 1,1,1-triethoxyethane, 1-methoxy-2-acetoxypropane, 4-methylpyridine, n,n-diethyl-1,2-ethanediamine, 2,6-dimethylmorpholine, 2-ethyl-1-butanol, 2-methyl-1-pentanol, methyl hexanoate, 2-propoxyethanol, 1-propoxy-2-propanol or dimethylethanolamine.

The organic extracting agent to be used may be chosen as a function of the compounds present in said first composition. Thus, the organic extracting agent may be chosen as a function of the separation factor and of the absorption capacity established for a particular composition. Besides these two criteria, the choice of the organic extracting agent may be optionally based on other commercial or environmental criteria, for instance the cost of the organic extracting agent, its availability on the market, and its toxicity or flammability properties. Furthermore, according to a particular embodiment, in order to optimize the functioning of the distillation columns used in the steps b) and c) of the present process for purifying 1,1,1,2,2-pentachloropropane, the boiling point of the organic extracting agent may be from 0° C. to 200° C., advantageously from 10° C. to 190° C., preferably from 10° C. to 180° C., in particular from 10° C. to 150° C., more particularly from 20° C. to 150° C., preferentially from 50° C. to 150° C. and even more preferentially from 75° C. to 150° C.

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of 1,1,1,2,2-pentafluoropropane in said organic extracting agent at infinite dilution;

P1 represents the saturating vapor pressure of 1,1,1,2,2-pentafluoropropane;

$\gamma_{2,S}$ represents the activity coefficient of said at least one compound consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) in said organic extracting agent at infinite dilution;

P2 represents the saturating vapor pressure of said at least one of the compounds consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

Advantageously, the separation factor $S_{1,2}$ is greater than or equal to 1.2, preferably greater than or equal to 1.4, more preferentially greater than or equal to 1.5, in particular greater than or equal to 1.8, more particularly greater than or equal to 1.9.

According to a preferred embodiment, said organic extracting agent has an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of said at least one of the compounds consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) in said organic extracting agent at infinite dilution. Advantageously, the absorption capacity $C_{2,S}$ is greater than or equal to 0.40, preferably greater than or equal to 0.60, more preferentially greater than or equal to 0.80, in particular greater than or equal to 0.90, more particularly greater than or equal to 1.0 and preferentially greater than or equal to 1.05.

Thus, said organic extracting agent may have a separation factor $S_{1,2}$ of greater than or equal to 1.1, advantageously greater than or equal to 1.2, preferably greater than or equal to 1.4, more preferentially greater than or equal to 1.5, in particular greater than or equal to 1.8 and more particularly greater than or equal to 1.9; and an absorption capacity $C_{2,S}$ of greater than or equal to 0.20, advantageously greater than or equal to 0.4, preferably greater than or equal to 0.60, more preferentially greater than or equal to 0.80, in particular greater than or equal to 0.90, more particularly greater than or equal to 1.0 and preferentially greater than or equal to 1.05.

Said first composition may be an azeotropic or quasi-azeotropic composition comprising 1,1,1,2,2-pentafluoropropane (245cb) and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

Said first composition may be an azeotropic or quasi-azeotropic composition comprising 1,1,1,2,2-pentafluoropropane (245cb) and at least two, at least three, at least four, at least five, at least six or all of the compounds chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf). The content of each of the compounds in the first azeotropic or quasi-azeotropic composition is as expressed above.

Depending on the compound(s) to be removed in said first composition, said separation factor and said absorption capacity may be calculated for a particular binary couple consisting of 1,1,1,2,2-pentafluoropropane (245cb) and one of the compounds chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf). Thus, to select said organic extracting agent that is suitable for use in the extractive distillation step b), the separation factor and the absorption capacity may be calculated, for example, for a 1,1,1,2,2-pentafluoropropane (245cb) and trans-1,3,3,3-tetrafluoro-1-propene (1234ze-E) binary couple if said first composition comprises these two compounds. The separation factor $S_{1,2}$ makes it possible to determine the capacity of an organic extracting agent to separate two or more compounds. The absorption capacity $C_{2,S}$ makes it possible to determine the amount of solvent to be used to obtain separation between the compounds under consideration. For all of the first compositions detailed below, said organic extracting agent may have a separation factor $S_{1,2}$ of greater than or equal to 1.1, advantageously greater than or equal to 1.2, preferably greater than or equal to 1.4, more preferentially greater than or equal to 1.5, in particular greater than or equal to 1.8 and more particularly greater than or equal to 1.9; and/or said organic extracting agent may have an absorption capacity $C_{2,S}$ of greater than or equal to 0.20, advantageously greater than or equal to 0.4, preferably greater than or equal to 0.5, more preferentially greater than or equal to 0.8, in particular greater than or equal to 0.9, more particularly greater than or equal to 1.0 and preferentially greater than or equal to 1.05.

In particular, said first composition may be an azeotropic or quasi-azeotropic composition comprising 1,1,1,2,2-pentafluoropropane (245cb) and trans-1,3,3,3-tetrafluoro-1-propene (1234ze-E). The content of each of the compounds in this particular composition is as expressed above with reference to the individual contents of each of the compounds. Said azeotropic or quasi-azeotropic composition may be obtained at a temperature of from −30° C. to 50° C. Said azeotropic or quasi-azeotropic composition may be obtained for a pressure of from 0.5 bar to 10 bar. Said azeotropic or quasi-azeotropic composition may be obtained for a weight content of 1,1,1,2,2-pentafluoropropane (245cb) relative to the total weight of the azeotropic or quasi-azeotropic composition. Thus, the second composition may comprise 1,1,1,2,2-pentafluoropropane (245cb), trans-1,3,3,3-tetrafluoro-1-propene (1234ze-E) and said organic extracting agent. Said organic extracting agent may have a separation factor $S_{1,2}$ of greater than or equal to 1.5, said separation factor being calculated by the formula $S_{1,2}=(\gamma_{1,S}*P1)/(\gamma_{2,S}*P2)$ in which $\gamma_{1,S}$ represents the activity coefficient of 1,1,1,2,2-pentafluoropropane relative to said organic extracting agent, P1 represents the saturating vapor pressure of 1,1,1,2,2-pentafluoropropene, $S_{2,S}$ represents the activity coefficient of trans-1,3,3,3-tetrafluoro-1-propene in said organic extracting agent at infinite dilution, and P2 represents the saturating vapor pressure of trans-1,3,3,3-tetrafluoro-1-propene. Said organic extracting agent may have an absorption capacity $C_{2,S}$ of greater than or equal to 0.6, said absorption capacity being calculated by the formula $C_{2,S}=1/(\gamma_{2,S})$ in which $\gamma_{2,S}$ represents the activity coefficient in said organic extracting agent at infinite dilution. Thus, to separate out the first azeotropic or quasi-azeotropic composition comprising 1,1,1,2,2-pentafluoropropane (245cb) and trans-1,3,3,3-tetrafluoro-1-propene (1234ze-E), an organic extracting agent with a separation factor $S_{1,2}$ of greater than or equal to 1.5 and an absorption capacity $C_{2,S}$ of greater than or equal to 0.6 may be used; said organic extracting agent may thus be ethylamine, acetaldehyde, isopropylamine, methyl formate, diethyl ether, 1,2-epoxypropane, ethylmethylamine, dimethoxymethane, 2-amino-2-methylpropane, methyl cyclopropyl ether, n-propylamine, isopropylmethylamine, 2-ethoxypropane, methyl t-butyl ether, diethylamine, propanone, methyl acetate, 4-methoxy-2-methyl-2-butanethiol, 2-butanamine, n-methylpropylamine, isobutanal, tetrahydrofuran, isopropyl formate, diisopropyl ether, 2-ethoxy-2-methylpropane, 1-butylamine, ethyl acetate, butanone, n-propyl formate, 2-ethoxybutane, 1-methoxy-2-methylbutane, 2,2-dimethoxypropane, 1-ethoxy-2-methylpropane, diisopropylamine, 1,2-dimethoxyethane, 3-methyl-2-butanamine, diethoxymethane, isopropyl acetate, di-n-propyl ether, 3-pentylamine, n-methylbutylamine, 1-ethoxybutane, 1-methoxy-2-propanamine, 2-methylbutanal, 2-methoxyethanamine, tert-butyl acetate, propionitrile, 2-allyloxyethanol, 1-methoxypentane, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, dipropylamine, 2-ethoxyethanamine, sec-butyl acetate, n-methyl-1,2-ethanediamine, 2,2-diethoxypropane, pyridine, 4-methyl-2-pentanone, 1,2-diaminoethane, butyronitrile, sec-butyl tert-butyl ether, 1-methoxy-2-propanol, 1,2-propanediamine, 2,6-dimethyl-5-heptenal, 1-(dimethylamino)-2-propanol, 3-methyl-3-pentanol, 1,1-diethoxypropane, 2-ethylbutylamine, diethyl carbonate, n-butyl acetate, 2-hexanone, n-ethylethylenediamine, 5-hexen-2-one, 2-methylpyridine, 2-methoxy-1-propanol, hexanal, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-methylpyrazine, 2-ethoxy-1-propanol, 1-methylpiperazine, 1,3-propanediamine, di-n-butyl ether, valeronitrile, 2-heptanamine, 1-ethoxyhexane, n,n-diethylethylenediamine, 2,6-dimethylpyridine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol or 1-propoxy-2-propanol.

Advantageously, said organic extracting agent may have a separation factor $S_{1,2}$ of greater than or equal to 1.8 and/or an absorption capacity $C_{2,S}$ of greater than or equal to 0.8. Said organic extracting agent may thus be ethylamine, isopropylamine, ethylmethylamine, 2-amino-2-methylpropane, n-propylamine, isopropylmethylamine, diethylamine, propanone, 2-butanamine, n-methylpropylamine, tetrahydrofuran, 1-butylamine, ethyl acetate, butanone, 1,2-dimethoxyethane, 3-methyl-2-butanamine, 3-pentylamine, n-methylbutylamine, 1-methoxy-2-propanamine, 2-methoxyethanamine, ethyl propionate, dioxane, 3-pentanone, 2-pentanone, 2-methoxy-1-propanamine, trimethoxymethane, n-pentylamine, 3,3-dimethyl-2-butanone, 1,3-dioxane, piperidine, 2-ethoxyethanamine, n-methyl-1,2-ethanediamine, 1,2-diaminoethane, butyronitrile, 1-methoxy-2-propanol, 1,2-propanediamine, 1-(dimethylamino)-2-propanol, 2-ethylbutylamine, diethyl carbonate, n-butyl acetate, 2-hexanone, n-ethylethylenediamine, 2-methoxy-1-propanol, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, 2-ethoxy-1-propanol, 1-methylpiperazine, 1,3-propanediamine, valeronitrile, 2-heptanamine, n,n-diethylethylenediamine, 4-methyl-2-hexanone, 1-methoxy-2-acetoxypropane, 4-methylpyridine, n,n'-diethyl-1,2-ethanediamine, 2,6-dimethylmorpholine, methyl hexanoate, 2-propoxyethanol or 1-propoxy-2-propanol.

Preferably, said organic extracting agent may have a separation factor $S_{1,2}$ of greater than or equal to 1.9 and/or an absorption capacity $C_{2,S}$ of greater than or equal to 0.9. Said organic extracting agent may thus be ethylamine, isopropylamine, ethylmethylamine, 2-amino-2-methylpropane, n-propylamine, isopropylmethylamine, diethylamine, propanone, 2-butanamine, n-methylpropylamine, tetrahydrofuran, 1-butylamine, ethyl acetate, butanone, 1,2-dimethoxyethane, 3-methyl-2-butanamine, 3-pentylamine, n-methylbutylamine, 1-methoxy-2-propanamine, 2-methoxyethanamine, ethyl propionate, dioxane, 3-pentanone, 2-pentanone, 2-methoxy-1-propanamine, n-pentylamine, 3,3-dimethyl-2-butanone, 1,3-dioxane, piperidine, 2-ethoxyethanamine, n-methyl-1,2-ethanediamine, 1,2-diaminoethane, 1,2-propanediamine, 1-(dimethylamino)-2-propanol, 2-ethylbutylamine, n-butyl acetate, 2-hexanone, n-ethylethylenediamine, 1-ethoxy-2-propanol, 4-methyl-2-hexanamine, hexylamine, 2-(dimethylamino)ethanol, cyclohexylamine, n-ethyl-2-dimethylaminoethylamine, 2-ethoxy-1-propanol, 1-methylpiperazine, 1,3-propanediamine, 2-heptanamine, n,n-diethylethylenediamine, 1-methoxy-2-acetoxypropane, 4-methylpyridine, n,n'-diethyl-1,2-ethanediamine, 2,6-dimethylmorpholine, methyl hexanoate or 1-propoxy-2-propanol.

Preferably, said organic extracting agent is chosen from the group consisting of ethylamine, isopropylamine, n-propylamine, diethylamine, propanone, tetrahydrofuran, ethyl acetate, butanone, 3-pentylamine, 2-methoxyethanamine, dioxane, 3-pentanone, 2-pentanone, n-pentylamine, 1,3-dioxane, 1,2-diaminoethane, 1,2-propanediamine, 2-methoxyethanol, n-butyl acetate and 1-ethoxy-2-propanol. In particular, the organic extracting agent is chosen from the group consisting of ethylamine, isopropylamine, n-propylamine, diethylamine, propanone, tetrahydrofuran, ethyl acetate, butanone, 3-pentylamine, 2-methoxyethanamine, dioxane, 3-pentanone, 2-pentanone, n-pentylamine, 1,3-dioxane, 1,2-diaminoethane, 1,2-propanediamine, 2-methoxyethanol, n-butyl acetate and 1-ethoxy-2-propanol. More particularly, said organic extracting agent is chosen from the group consisting of ethylamine, isopropylamine, n-propylamine, diethylamine, tetrahydrofuran, ethyl acetate, butanone, 3-pentylamine, 2-methoxyethanamine, dioxane, 2-pentanone, n-pentylamine, 1,3-dioxane, 1,2-diaminoethane, 1,2-propanediamine and 1-ethoxy-2-propanol.

According to a particular embodiment, said first composition may be an azeotropic or quasi-azeotropic composition comprising 1,1,1,2,2-pentafluoropropane (245cb) and cis-1,3,3,3-tetrafluoro-1-propene (1234ze-Z). The content of each of the compounds in this particular composition is as expressed above with reference to the individual contents of each of the compounds. Thus, the second composition may comprise 1,1,1,2,2-pentafluoropropane (245cb), cis-1,3,3,3-tetrafluoro-1-propene (1234ze-Z) and said organic extracting agent, preferably having a separation factor $S_{1,2}$ of greater than or equal to 1.1, advantageously greater than or equal to 1.2, preferably greater than or equal to 1.4, more preferentially greater than or equal to 1.5, in particular greater than or equal to 1.8 and more particularly greater than or equal to 1.9; and/or said organic extracting agent may have an absorption capacity $C_{2,S}$ of greater than or equal to 0.20, advantageously greater than or equal to 0.4, preferably greater than or equal to 0.5, more preferentially greater than or equal to 0.8, in particular greater than or equal to 0.9, more particularly greater than or equal to 1.0 and preferentially greater than or equal to 1.05. Said organic extracting agent may be as defined above for the first composition comprising 1,1,1,2,2-pentafluoropropane (245cb) and trans-1,3,3,3-tetrafluoro-1-propene (1234ze-E).

According to a particular embodiment, said first composition may be an azeotropic or quasi-azeotropic composition comprising 1,1,1,2,2-pentafluoropropane (245cb) and 1,1-difluoroethane (152a). The content of each of the compounds in this particular composition is as expressed above with reference to the individual contents of each of the compounds. Thus, the second composition may comprise 1,1,1,2,2-pentafluoropropane (245cb), 1,1-difluoroethane (152a) and said organic extracting agent, preferably having a separation factor $S_{1,2}$ of greater than or equal to 1.1, advantageously greater than or equal to 1.2, preferably greater than or equal to 1.4, more preferentially greater than or equal to 1.5, in particular greater than or equal to 1.8 and more particularly greater than or equal to 1.9; and/or said organic extracting agent may have an absorption capacity $C_{2,S}$ of greater than or equal to 0.20, advantageously greater than or equal to 0.4, preferably greater than or equal to 0.5, more preferentially greater than or equal to 0.8 and in particular greater than or equal to 0.9. Said organic extracting agent may be as defined above for the first composition comprising 1,1,1,2,2-pentafluoropropane (245cb) and trans-1,3,3,3-tetrafluoro-1-propene (1234ze-E).

According to a particular embodiment, said first composition may be an azeotropic or quasi-azeotropic composition comprising 1,1,1,2,2-pentafluoropropane (245cb) and 1,1,1,2-tetrafluoroethane (134a). The content of each of the compounds in this particular composition is as expressed above with reference to the individual contents of each of the compounds. Thus, the second composition may comprise 1,1,1,2,2-pentafluoropropane (245cb), 1,1,1,2-tetrafluoroethane (134a) and said organic extracting agent, preferably having a separation factor $S_{1,2}$ of greater than or equal to 1.1, advantageously greater than or equal to 1.2, preferably greater than or equal to 1.4, more preferentially greater than or equal to 1.5, in particular greater than or equal to 1.8 and more particularly greater than or equal to 1.9; and/or said organic extracting agent may have an absorption capacity $C_{2,S}$ of greater than or equal to 0.20, advantageously greater than or equal to 0.4, preferably greater than or equal to 0.5, more preferentially greater than or equal to 0.8 and in particular greater than or equal to 0.9. Said organic extracting agent may be as defined above for the first composition comprising 1,1,1,2,2-pentafluoropropane (245cb) and trans-1,3,3,3-tetrafluoro-1-propene (1234ze-E). According to a particular embodiment, said first composition may be an azeotropic or quasi-azeotropic composition comprising 1,1,1,2,2-pentafluoropropane (245cb) and trans-1,2,3,3,3-pentafluoropropene (1225ye-E). The content of each of the compounds in this particular composition is as expressed above with reference to the individual contents of each of the compounds. Thus, the second composition may comprise 1,1,1,2,2-pentafluoropropane (245cb), trans-1,2,3,3,3-pentafluoropropene (1225ye-E) and said organic extracting agent, preferably having a separation factor $S_{1,2}$ of greater than or equal to 1.1, advantageously greater than or equal to 1.2, preferably greater than or equal to 1.4, more preferentially greater than or equal to 1.5, in particular greater than or equal to 1.8 and more particularly greater than or equal to 1.9; and/or said organic extracting agent may have an absorption capacity $C_{2,S}$ of greater than or equal to 0.20, advantageously greater than or equal to 0.4, preferably greater than or equal to 0.5, more preferentially greater than or equal to 0.8 and in particular greater than or equal to 0.9. Said organic extracting agent may be as defined above for the first composition comprising 1,1,1,2,2-pentafluoropropane (245cb) and trans-1,3,3,3-tetrafluoro-1-propene (1234ze-E).

According to a particular embodiment, said first composition may be an azeotropic or quasi-azeotropic composition comprising 1,1,1,2,2-pentafluoropropane (245cb) and cis-1,2,3,3,3-pentafluoropropene (1225ye-Z). The content of each of the compounds in this particular composition is as expressed above with reference to the individual contents of each of the compounds. Thus, the second composition may comprise 1,1,1,2,2-pentafluoropropane (245cb), cis-1,2,3,3,3-pentafluoropropene (1225ye-Z) and said organic extracting agent, preferably having a separation factor $S_{1,2}$ of greater than or equal to 1.1, advantageously greater than or equal to 1.2, preferably greater than or equal to 1.4, more preferentially greater than or equal to 1.5, in particular greater than or equal to 1.8 and more particularly greater than or equal to 1.9; and/or said organic extracting agent may have an absorption capacity $C_{2,S}$ of greater than or equal to 0.20, advantageously greater than or equal to 0.4, preferably greater than or equal to 0.5, more preferentially greater than or equal to 0.8 and in particular greater than or equal to 0.9. Said organic extracting agent may be as defined above for the first composition comprising 1,1,1,2,2-pentafluoropropane (245cb) and trans-1,3,3,3-tetrafluoro-1-propene (1234ze-E).

According to a particular embodiment, said first composition may be an azeotropic or quasi-azeotropic composition comprising 1,1,1,2,2-pentafluoropropane (245cb) and 3,3,3-trifluoropropene (1243zf). The content of each of the compounds in this particular composition is as expressed above with reference to the individual contents of each of the compounds. Thus, the second composition may comprise 1,1,1,2,2-pentafluoropropane (245cb), 3,3,3-trifluoropropene (1243zf) and said organic extracting agent, preferably having a separation factor $S_{1,2}$ of greater than or equal to 1.1, advantageously greater than or equal to 1.2, preferably greater than or equal to 1.4, more preferentially greater than or equal to 1.5, in particular greater than or equal to 1.8 and more particularly greater than or equal to 1.9; and/or said organic extracting agent may have an absorption capacity $C_{2,S}$ of greater than or equal to 0.20, advantageously greater than or equal to 0.4, preferably greater than or equal to 0.5, more preferentially greater than or equal to 0.8 and in particular greater than or equal to 0.9. Said organic extracting agent may be as defined above for the first composition comprising 1,1,1,2,2-pentafluoropropane (245cb) and trans-1,3,3,3-tetrafluoro-1-propene (1234ze-E).

According to a preferred embodiment, said third composition comprising the organic extracting agent and said at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) may be subjected to distillation to separate the organic extracting agent and said at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

According to a particular embodiment, the stream comprising 1,1,1,2,2-pentafluoropropane separated out in step b) of the present process is recovered to be used in a process for producing 2,3,3,3-tetrafluoropropene. Preferably, in this embodiment, traces of organic extracting agent may be present in the stream comprising 1,1,1,2,2-pentafluoropropane. Preferably, the organic extracting agent is chosen so as not to impair the performance of the catalyst used in the process for producing 2,3,3,3-tetrafluoropropene.

The present process thus makes it possible to purify 1,1,1,2,2-pentafluoropropane. Advantageously, the content of at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) in the stream comprising 1,1,1,2,2-pentafluoropropane, obtained in step b) of the present purification process, is less than the content of that or those in said first composition. For example, the content of any one of the compounds may be reduced by 50%, advantageously by 75%, preferably by 90%, in particular by 95% and more particularly by 98%. Advantageously, the content of at least two, at least three, at least four, at least five or of all of the compounds chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) may be reduced by 50%, advantageously by 75%, preferably by 90%, in particular by 95% and more particularly by 98%. Preferably, the stream comprising 1,1,1,2,2-pentafluoropropane obtained in step b) of the present purification process may be free of at least one, at least two, at least three, at least four, at least five or of all of the compounds chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) when this or these compounds are present in said first composition. In particular, the stream comprising 1,1,1,2,2-pentafluoropropane obtained in step b) of the present purification process may be free of trans-1,3,3,3-tetrafluoro-1-propene (1234ze-E). The term "free of" means that the stream comprising 1,1,1,2,2-pentafluoropropane comprises less than 50 ppm, advantageously less than 20 ppm and preferably less than 10 ppm of the compound under consideration relative to the total weight of the stream.

According to a preferred embodiment, said first composition used in step a) of the present purification process is obtained from a composition of 2,3,3,3-tetrafluoro-1-propene (1234yf). The 2,3,3,3-tetrafluoro-1-propene (1234yf) composition may be purified beforehand, before being used in the present process for purifying 1,1,1,2,2-pentafluoropropane. Thus, the present process may comprise, before step a), the following steps:

i') implementation of a composition A comprising 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf), and, optionally or not, impurities with a boiling point below the boiling point of 2,3,3,3-tetrafluoro-1-propene;

ii') optionally or not, distillation of said composition of 2,3,3,3-tetrafluoro-1-propene to remove, at the top of the column, impurities with a boiling point below the boiling point of 2,3,3,3-tetrafluoro-1-propene and to form a first stream comprising 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), pentafluoropropene (1225ye-Z) and 3,3,3-trifluoropropene (1243zf) recovered at the bottom of the distillation column;

iii') distillation of said first stream recovered at the bottom of the distillation column in step ii') or of composition A to recover, at the top of the distillation column, a second stream comprising 2,3,3,3-tetrafluoro-1-propene and to recover, at the bottom of the distillation column, a third stream comprising 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) corresponding to said first composition used in step a) of the process for purifying 1,1,1,2,2-pentafluoropropane according to the present invention.

Said impurities with a boiling point below the boiling point of 2,3,3,3-tetrafluoro-1-propene may be trifluoromethane (F23), monofluoromethane (F41), difluoromethane (F32), pentafluoroethane (F125), 1,1,1-trifluoroethane (F143a), trifluoropropyne or 1-chloropentafluoroethane (F115).

According to a second aspect, the present invention provides a process for producing 2,3,3,3-tetrafluoro-1-propene. In addition, this process may include the purification of the 1,1,1,2,2-pentafluoropropane produced during the production of 2,3,3,3-tetrafluoro-1-propene. Thus, the present invention provides a process for producing 2,3,3,3-tetrafluoro-1-propene, comprising the steps of:

A) fluorination in the presence of a catalyst of a compound of formula $CX(Y)_2$—$CX(Y)_m$—$CH_mXY$ (I) in which X and Y independently represent H, F or Cl and m=0 or 1; and/or fluorination in the presence of a catalyst of a compound of formula $(CX_nY_{3-m})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream comprising 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf);

C) distillation of the stream recovered in step B) and recovery, at the top of the distillation column, of a stream comprising 2,3,3,3-tetrafluoro-1-propene, and, at the bottom of the distillation column, a stream comprising 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf);

D) implementation of the process for purifying 1,1,1,2,2-pentafluoropropane according to the present invention using the stream recovered at the bottom of the distillation column in step C); and E) recycling into step A) of the stream comprising 1,1,1,2,2-pentafluoropropane formed in step b) of the process performed in step D) or dehydrofluorination of the stream comprising 1,1,1,2,2-pentafluoropropane formed in step b) of the process for purifying 1,1,1,2,2-pentafluoropropane performed in step D) in the absence or presence of hydrofluoric acid.

The reactions of step A) may be performed in the presence of hydrofluoric acid.

The stream comprising 1,1,1,2,2-pentafluoropropane used to perform step D) may correspond to said first composition described above in relation with the process for purifying 1,1,1,2,2-pentafluoropropane. The stream comprising 1,1,1,2,2-pentafluoropropane obtained at the bottom of the distillation column in step C) and used to perform step D) may also comprise at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

According to a preferred embodiment, the process for producing 2,3,3,3-tetrafluoro-1-propene comprising the steps of:
A) fluorination in the presence of a catalyst of a compound of formula $CX(Y)_2-CX(Y)_m-CH_mXY$ (I) in which X and Y independently represent H, F or Cl and m=0 or 1; and/or fluorination in the presence of a catalyst of a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;
B) recovery of a stream comprising 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf);
C) distillation of the stream recovered in step B) and recovery, at the top of the distillation column, of a stream comprising 2,3,3,3-tetrafluoro-1-propene, and, at the bottom of the distillation column, a stream comprising 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf);
D) implementation of the process for purifying 1,1,1,2,2-pentafluoropropane using the stream recovered at the bottom of the distillation column in step C), comprising the steps of:
a) placing the stream comprising 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) in contact with at least one organic extracting agent, to form a second composition;
b) extractive distillation of said second composition to form and recover:
i) a third composition comprising said organic extracting agent and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf); and
ii) a stream comprising 1,1,1,2,2-pentafluoropropane;
c) recovery of said third composition and separation between said organic extracting agent and said at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf);
E) recycling into step A) of the stream comprising 1,1,1,2,2-pentafluoropropane formed and recovered in step b) of the purification process performed in step D) or dehydrofluorination of the stream comprising 1,1,1,2,2-pentafluoropropane formed in step b) of the process for purifying 1,1,1,2,2-pentafluoropropane performed in step D) in the absence or presence of hydrofluoric acid.

According to a particular embodiment, the stream recovered in step B) of the process for producing 2,3,3,3-tetrafluoro-1-propene may comprise hydrofluoric acid. In this case, prior to step C), the stream recovered in step B) may undergo a preliminary distillation B1') to remove HF at the bottom of the distillation column. A stream comprising 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) is recovered at the top of the distillation column. The latter stream recovered at the top of the distillation column is then subjected to step C) of the process for producing 2,3,3,3-tetrafluoro-1-propene.

According to a particular embodiment, the stream recovered in step B) of the process for producing 2,3,3,3-tetrafluoro-1-propene may also comprise impurities with a boiling point below the boiling point of 2,3,3,3-tetrafluoro-1-propene. In this case, prior to step C), the stream recovered in step B) may undergo a preliminary distillation B2'), subsequent to step B1'), to remove, at the top of the distillation column, said impurities with a boiling point below the boiling point of 2,3,3,3-tetrafluoro-1-propene and to form a first stream comprising 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) recovered at the bottom of the distillation column. The latter stream recovered at the bottom of the distillation column is then subjected to step C) of the process for producing 2,3,3,3-tetrafluoro-1-propene.

According to a particular embodiment, the stream recovered in step B) of the process for producing 2,3,3,3-tetrafluoro-1-propene may also comprise HCl. The hydrochloric acid may be recovered by distillation before or after step B1', independently of the other steps of the process.

More particularly, step A) is performed using 1,1,2,3-tetrachloropropene, 2,3,3,3,-tetrachloropropene, 1,1,3,3-tetrachloropropene, 1,3,3,3-tetrachloropropene, 1,1,1,2,3-pentachloropropane, 1,1,1,3,3-pentachloropropane, 1,1,2,2,3-pentachloropropane, 1,2-dichloro-3,3,3-trifluoropropane, 2-chloro-2,3,3,3-tetrafluoropropane, 1,1,1,2,2-pentafluoropropane, 1-chloro-1,3,3,3-tetrafluoropropane and 1,1,1,3,3-pentafluoropropane, preferably using 1,1,1,2,3-pentachloropropane, 1,1,2,3,tetrachloropropene, 1,1,1,2,2-pentafluoropropane and/or 2-chloro-3,3,3-trifluoro-1-propene; in particular using 1,1,1,2,3-pentachloropropane (240db).

FIG. 1a schematically represents a simplified scheme of a device for performing a process for purifying 1,1,1,2,2-pentafluoropropane according to a particular embodiment of the invention. The mixture derived from the fluorination reaction, in the presence of a catalyst, of a compound of formula $CX(Y)_2$—$CX(Y)_m$—$CH_mXY$ in which X and Y independently represent H, F or Cl and m=0 or 1; and/or from fluorination, in the presence of a catalyst, of a compound of formula $(CX_nY_{3-n})CH_pX_{1-p}$=$CH_mX_{2-m}$ (II) is obtained in 1. The mixture comprises, in this particular embodiment, 2,3,3,3-tetrafluoro-1-propene, 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf), and impurities with a boiling point below the boiling point of 2,3,3,3-tetrafluoro-1-propene. The mixture is transferred into a distillation column 2 via pipe 10. The impurities with a boiling point below that of 2,3,3,3-tetrafluoro-1-propene are recovered at the top of distillation column 2 and conveyed via pipe 11 to an incinerator or a purification device 7. The residue obtained at the bottom of the distillation column and comprising the other constituents of the mixture is conveyed to a second distillation column 3 via pipe 12. The distillation performed in 3 is directed toward separating 2,3,3,3-tetrafluoro-1-propene from the other constituents of the mixture. The distillation operating conditions are thus suitable for this purpose. 2,3,3,3-Tetrafluoro-1-propene is recovered at the top of the distillation column and conveyed via pipe 17 to a purification device 4 that is capable of terminating the purification of the 2,3,3,3-tetrafluoro-1-propene, for example a distillation column. The mixture recovered at the bottom of the distillation column 3 especially comprises 1,1,1,2,2-pentafluoropropane and at least one compound chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf). This mixture is transferred via pipe 13 into an extractive distillation device 5 to separate the 1,1,1,2,2-pentafluoropropane from at least one of the following compounds: 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf), in particular to separate out trans-1,3,3,3-tetrafluoro-1-propene. The extractive distillation device 5 is fed with the organic extracting agent 19 chosen according to the method described in the present patent application. 1,1,1,2,2-Pentafluoropropane is recovered at the top of the extractive distillation device 5 and conveyed via pipe 8 to a device 18 for producing 2,3,3,3-tetrafluoro-1-propene. The mixture recovered at the bottom of the extractive distillation device 5 especially comprises the organic extracting agent 19 and at least one of the following compounds: 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf), in particular trans-1,3,3,3-tetrafluoro-1-propene. The mixture recovered at the bottom of the extractive distillation device 5 is conveyed via pipe at 14 to a distillation device 6 which is directed toward separating the organic extracting agent from the other compounds present. The organic extracting agent is recovered at the bottom of the distillation device and recycled via pipe 15 to the extractive distillation device 5. The compounds recovered at the top of the distillation device 6 are conveyed via pipe 16 to pipe 11 to be incinerated or purified in 7.

Figure 1B:
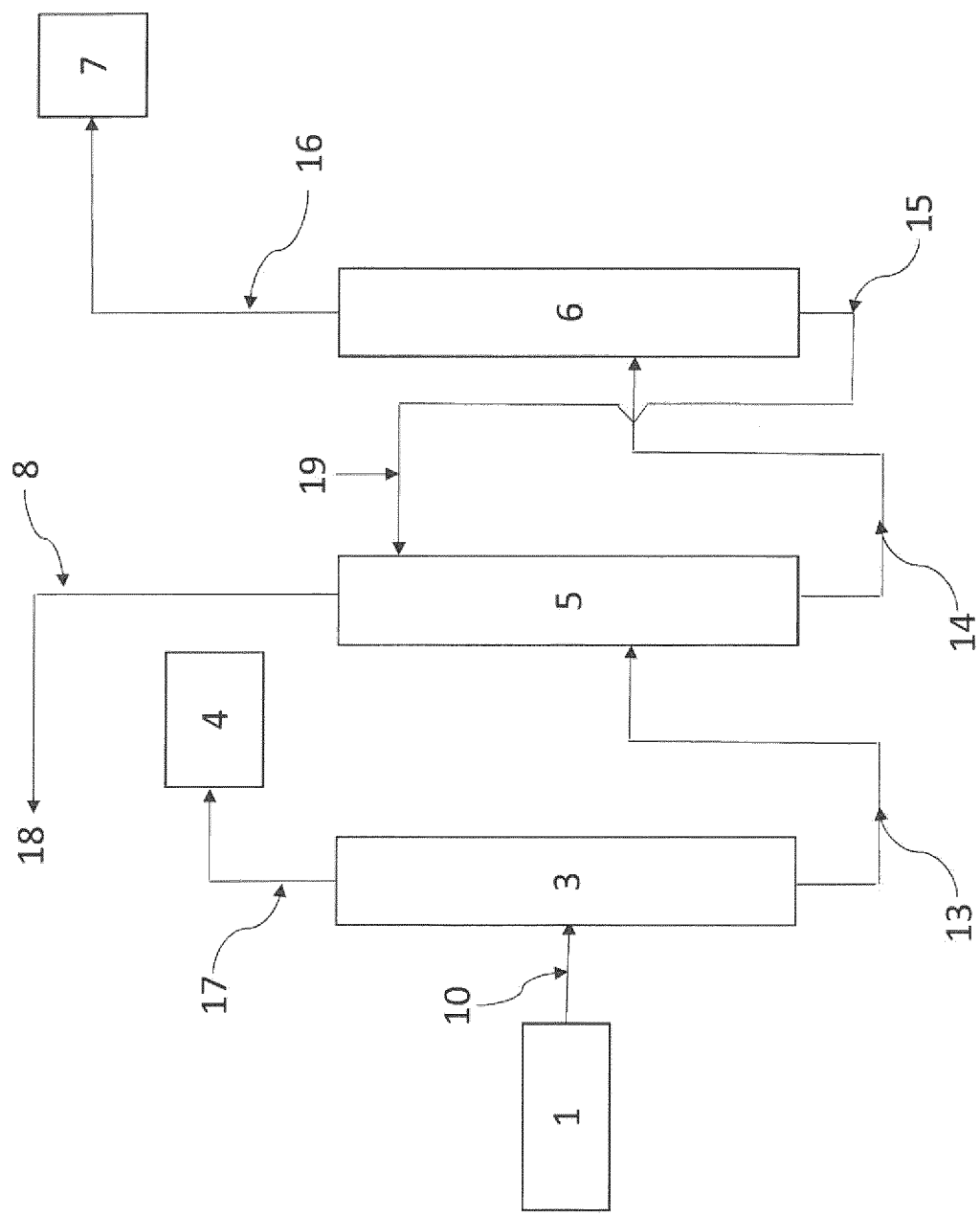
Figure 1C:
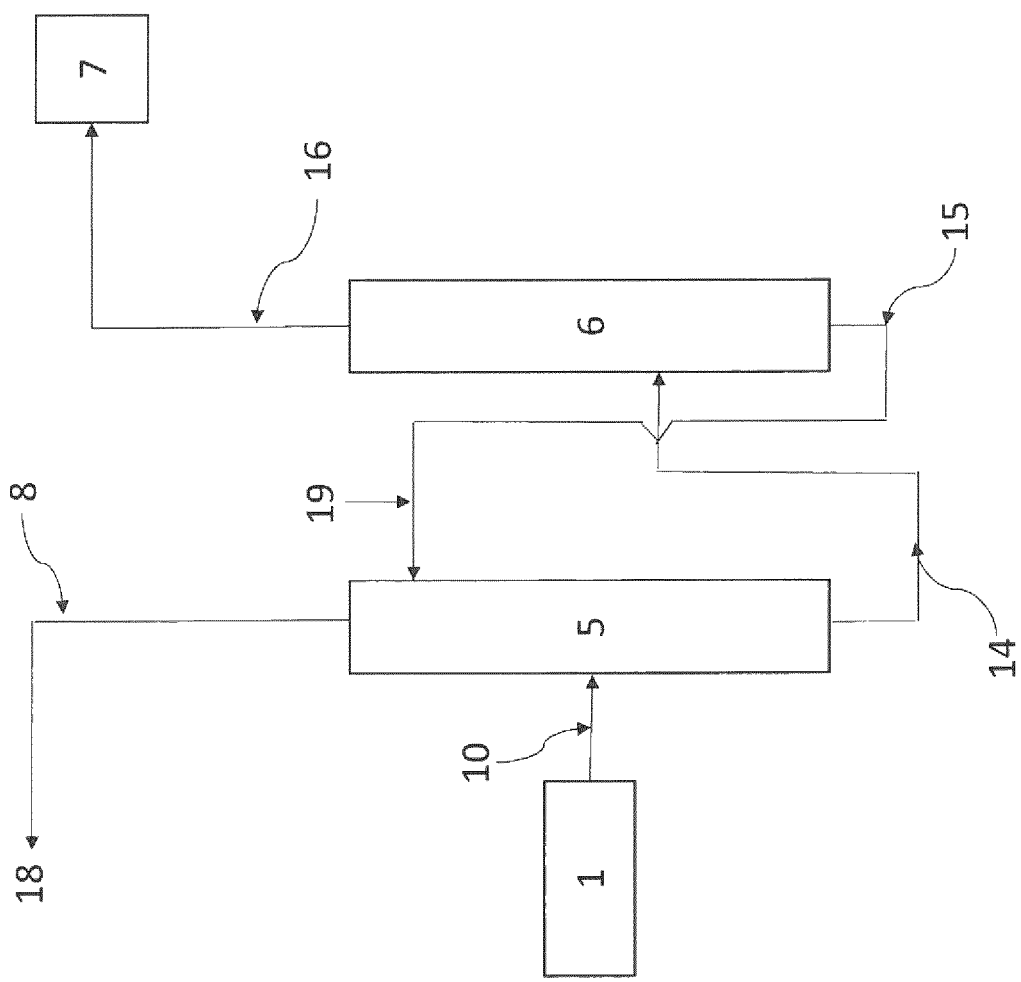

The mixture provided in 1 may be free of impurities with a boiling point below that of 2,3,3,3-tetrafluoro-1-propene. In this case, as illustrated in FIG. 1b, the mixture is conveyed via pipe 10 to the distillation column 3 to be processed as explained above in relation with FIG. 1a. In another particular embodiment illustrated in FIG. 1c, the mixture 1 may comprise 1,1,1,2,2-pentafluoropropane and at least one of the following compounds: 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf). In this case, the mixture is conveyed directly to the extractive distillation column 5 to be processed therein as explained above in relation with FIG. 1a.

Figure 2:
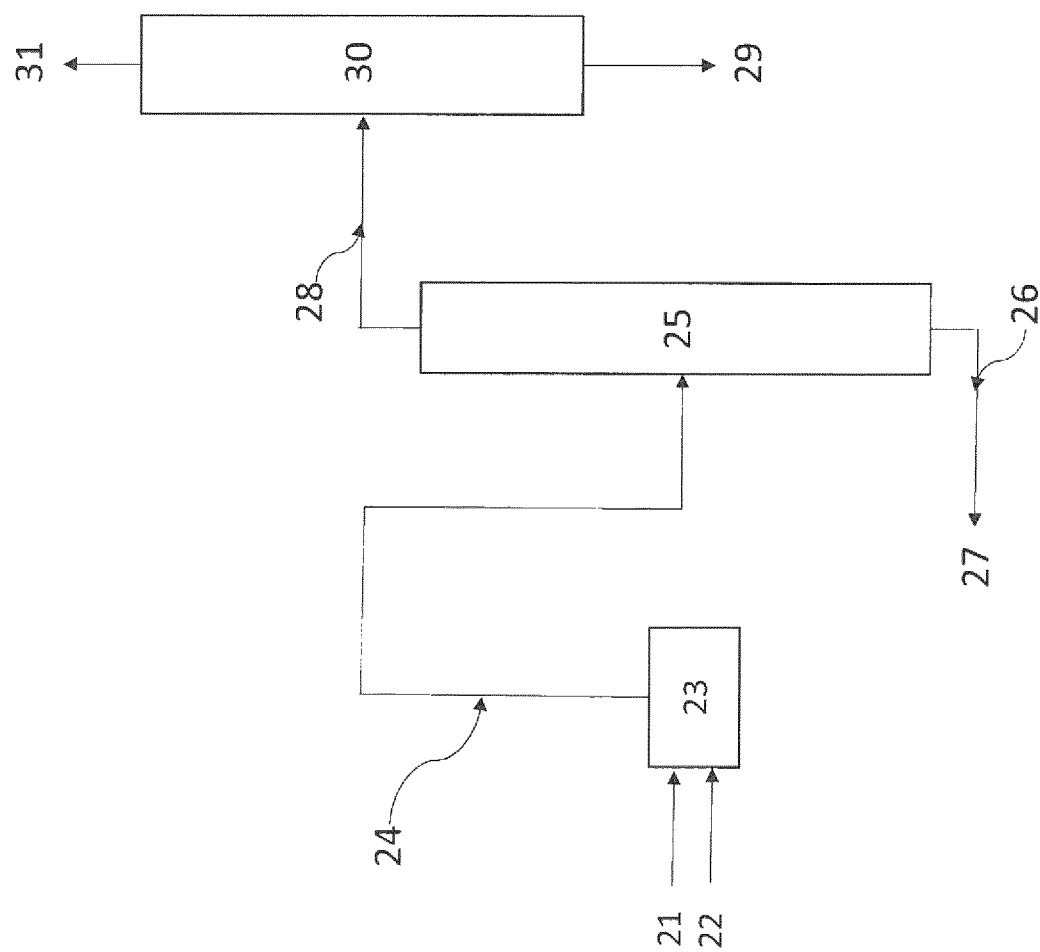
FIG. 2 schematically represents a device for performing a process for producing 2,3,3,3-tetrafluoropropene according to a particular embodiment of the present invention.

FIG. 2 schematically illustrates a device for performing a process for producing 2,3,3,3-tetrafluoropropene according to a particular embodiment of the present invention. Hydrofluoric acid 21 is placed in contact with 1,1,1,2,3-pentachloropropane (240db) 22 in a reactor 23. The mixture obtained and comprising 2,3,3,3-tetrafluoropropene, 1,1,1,2,2-pentafluoropropane (245cb) and at least one of the following compounds: 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) is recovered at the reactor outlet and conveyed to a distillation column 25 via pipe 24. The mixture may thus comprise HCl, HF and heavy impurities or impurities with a boiling point below that of 2,3,3,3-tetrafluoro-1-propene. The stream obtained at the bottom of the distillation column comprising HF and optionally heavy impurities is conveyed to the purification device 27 via pipe 26 to purify HF which will optionally be recycled in 23. The other constituents of the mixture are conveyed via pipe 28 to a distillation column 30. The stream at 31 obtained at the top of the distillation column contains HCl and the stream obtained at the bottom of the distillation column is conveyed to a purification device 29 four purifying 1,1,1,2,2-pentafluoropropane. The purification device 29 may be any of the devices illustrated in FIGS. 1a-1b.

The catalyst used in the present process for producing 2,3,3,3-tetrafluoropropene may be based, for example, on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments) and chromium fluorides, and mixtures thereof. Other possible catalysts are catalysts supported on carbon, antimony-based catalysts, and aluminum-based catalysts (for example $AlF_3$ and $Al_2O_3$, aluminum oxyfluoride and aluminum fluoride).

Use may be made in general of a chromium oxyfluoride, an aluminum fluoride or oxyfluoride, or an optionally supported catalyst containing a metal such as Cr, Ni, Fe, Zn, Ti, V, Zr, Mo, Ge, Sn, Pb, Mg or Sb.

Reference may be made in this respect to WO 2007/079431 (on page 7, lines 1-5 and 28-32) and EP 939071 (paragraph [0022]), WO 2008/054781 (on page 9, line 22 to page 10, line 34) and WO 2008/040969 (claim 1), to which reference is expressly made.

The catalyst is more particularly preferably chromium-based and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example about 1. The catalyst may contain from 0.5% to 20% by weight of nickel.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, for example described in U.S. Pat. No. 4,902,838, or obtained via the activation process described above.

The catalyst may comprise chromium and nickel in an activated or unactivated form, on a support which has optionally been subjected to activation.

Reference may be made to WO 2009/118628 (especially on page 4, line 30 to page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to activation with air, oxygen or chlorine and/or with HF.

For example, the catalyst is preferably subjected to activation with air or oxygen and HF at a temperature from 100 to 500° C., preferably from 250 to 500° C. and more particularly from 300 to 400° C. The activation time is preferably from 1 to 200 hours and more particularly from 1 to 50 hours.

This activation may be followed by a final fluorination activation step in the presence of an oxidizing agent, HF and organic compounds.

The HF/organic compounds mole ratio is preferably from 2 to 40 and the oxidizing agent/organic compounds mole ratio is preferably from 0.04 to 25. The temperature of the final activation is preferably from 300 to 400° C. and its duration is preferably from 6 to 100 hours.

The gas-phase fluorination reaction may be performed:
with an HF/compound of formula (I) and/or (II) mole ratio from 3:1 to 150:1, preferably from 4:1 to 125:1 and more particularly preferably from 5:1 to 100:1;
with a contact time from 3 to 100 seconds, preferably 4 to 75 seconds and more particularly 5 to 50 seconds (volume of catalyst divided by the total entering stream, adjusted to the operating temperature and pressure);
at a pressure ranging from atmospheric pressure to 20 bar, preferably from 2 to 18 bar and more particularly from 3 to 15 bar;
at a temperature (temperature of the catalytic bed) from 200 to 450° C., preferably from 250 to 400° C. and more particularly from 280 to 380° C.

The duration of the reaction step is typically from 10 to 8000 hours, preferably from 50 to 5000 hours and more particularly preferably from 70 to 1000 hours.

An oxidizing agent, preferably oxygen, may optionally be added during the fluorination reaction. The oxygen/organic compounds mole ratio may be from 0.005 to 2, preferably from 0.01 to 1.5. Oxygen may be introduced in pure form or in the form of air or an oxygen/nitrogen mixture. Oxygen may also be replaced with chlorine.

According to another aspect of the present invention, an azeotropic or quasi-azeotropic composition is provided. Said composition comprises from 50% to 99.99% by weight of 1,1,1,2,2-pentafluoropropane and less than 50% by weight of trans-1,3,3,3-tetrafluoro-1-propene relative to the total weight of the composition. Preferably, said composition also comprises at least one of the compounds chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf). Said at least one of the compounds chosen from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) may be present in the azeotropic composition in the proportions expressed above relative to the total weight of the composition. Said azeotropic or quasi-azeotropic composition may be obtained at a temperature of from −30° C. to 50° C. Said azeotropic or quasi-azeotropic composition may be obtained for a pressure of from 0.5 bar to 10 bar.

Method for Selecting the Organic Extracting Agent

The selection of the organic extracting agent is determined by using the Cosmo-RS model implemented in the COSMOTHERM software. For this selected binary couple, a separation factor is calculated for each of the solvents studied via the following equation:

$$S_{1,2} = (\gamma_{1,S} * P1)/(\gamma_{2,S} * P2) \text{ in which}$$

$\gamma_{1,S}$ represents the activity coefficient of the first compound 1 in the organic extracting agent under consideration at infinite dilution, P1 represents the saturating vapor pressure of the first compound 1, $\gamma_{2,S}$ represents the activity coefficient of the second compound 2 of the binary couple in the organic extracting agent under consideration at infinite dilution, P2 represents the saturating vapor pressure of the second compound.

An absorption capacity is also calculated for each of the solvents studied and for a binary couple (1,2) under consideration. The absorption capacity is calculated via the formula $C_{2,S} = 1/(\gamma_{2,S})$ in which $\gamma_{2,S}$ represents the activity coefficient of the second compound of the binary couple under consideration in said organic extracting agent studied at infinite dilution.

The calculations are repeated for each organic extracting agent studied. Minimum separation factor and absorption capacity values are identified so as to allow a sufficient separation between the first compound and the second compound of the binary couple (1,2) under consideration. The saturating vapor pressure is considered for a temperature of 25° C.

EXAMPLES

Example 1

In this example, separation between 1,1,1,2,2-pentafluoropropane (245cb) and trans-1,3,3,3-tetrafluoro-1-propene is considered. On the basis of the information obtained by the Cosmo-RS model, the solvents given in table 1 below were tested for the extractive distillation of a mixture comprising 1,1,1,2,2-pentafluoropropane (245cb) and trans-1,3,3,3-tetrafluoro-1-propene.

TABLE 1 capacity and separation factor of the organic extracting agent

| Organic extracting agent | Absorption capacity | Separation factor |
|---|---|---|
| Ethylamine | 1.95 | 3.60 |
| Isopropylamine | 1.85 | 3.14 |
| n-Propylamine | 1.86 | 3.14 |
| Diethylamine | 1.57 | 2.18 |
| Tetrahydrofuran | 1.73 | 1.90 |
| Ethyl acetate | 1.30 | 1.87 |
| Butanone | 1.07 | 1.84 |
| 3-Pentylamine | 1.62 | 2.39 |
| 2-Methoxyethanamine | 1.98 | 3.80 |
| Dioxane | 1.09 | 1.92 |
| n-Pentylamine | 1.64 | 2.71 |
| 1,3-Dioxane | 1.09 | 1.93 |
| 1,2-Diaminoethane | 1.28 | 6.88 |
| 2-Methoxyethanol | 0.57 | 2.05 |
| 1,2-Propanediamine | 1.50 | 4.92 |
| n-Butyl acetate | 1.35 | 1.86 |
| 1-Ethoxy-2-propanol | 1.12 | 2.15 |

The results were confirmed using a mixture comprising 70% to 90% by weight of 1,1,1,2,2-pentafluoropropane and 10% to 30% by weight of trans-1,3,3,3-tetrafluoro-1-propene relative to the total weight of the composition. The rest of the composition is formed by the organic extracting agent tested.

The invention claimed is:

1. A process for purifying 1,1,1,2,2-pentafluoropropane (245cb) from a first composition comprising 1,1,1,2,2-pentafluoropropane and at least one compound selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf), said process comprising:
  a) placing said first composition in contact with at least one organic extracting agent to form a second composition; wherein said at least one organic extracting agent comprises a solvent selected from the group consisting of ethylamine, isopropylamine, ethylmethylamine, 2-amino-2-methylpropane, n-propylamine, isopropylmethylamine, diethylamine, propanone, 2-butanamine, n-methylpropylamine, 1-butylamine, 1,2-dimethoxyethane, 3-methyl-2-butanamine, 3-pentylamine, n-methylbutylamine, 1-methoxy-2-propanamine, 2-methoxyethanamine, ethyl propionate, 2-pentanone, 2-methoxy-1-propanamine, n-pentylamine, 3,3-dimethyl-2-butanone, piperidine, 2-ethoxyethanamine, n-methyl-1,2-ethanediamine, 1,2-diaminoethane, 1,2-propanediamine, 1-(dimethylamino)-2-propanol, 2-ethylbutylamine, n-ethylethylenediamine, 1-ethoxy-2-propanol, 4-methyl-2-hexanamine, hexylamine, 2-(dimethylamino)ethanol, cyclohexylamine, n-ethyl-2-dimethylaminoethylamine, 2-ethoxy-1-propanol, 1-methylpiperazine, 1,3-propanediamine, 2-heptanamine, n,n-diethylethylenediamine, 1-methoxy-2-acetoxypropane, 4-methylpyridine, n,n'-diethyl-1,2-ethanediamine, 2,6-dimethylmorpholine, methyl hexanoate or 1-propoxy-2-propanol;
  b) distilling said second composition by extractive distillation to form:
    i) a third composition comprising said organic extracting agent and at least one compound selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf); and
    ii) a stream comprising 1,1,1,2,2-pentafluoropropane;
  c) recovering and separating said third composition to form a stream comprising said organic extracting agent and a stream comprising said at least one compound selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

2. The process as claimed in claim 1, wherein said organic extracting agent has a boiling point of between 10 and 150° C.

3. The process as claimed in claim 1, wherein said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$, wherein
  $\gamma_{1,S}$ represents the activity coefficient of 1,1,1,2,2-pentafluoropropane in said organic extracting agent at infinite dilution;
  P1 represents the saturating vapor pressure of 1,1,1,2,2-pentafluoropropane;
  $\gamma_{2,S}$ represents the activity coefficient of said at least one compound selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) in said organic extracting agent at infinite dilution;
  P2 represents the saturating vapor pressure of said at least one of the compound selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

4. The process as claimed in claim 1, wherein said organic extracting agent has an absorption capacity $C_{2,S}$ of greater than or equal to 0.20, said absorption capacity being calculated by the formula $C_{2,S}=1/(\gamma_{2,S})$, wherein $\gamma_{2,S}$ represents the activity coefficient of said at least one compound selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf) in said organic extracting agent at infinite dilution.

5. The process as claimed in claim 1, wherein said first composition comprises an azeotropic or quasi-azeotropic composition comprising 1,1,1,2,2-pentafluoropropane (245cb) and said at least one compound selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf).

6. The process as claimed in claim 1, wherein the first composition comprises an azeotropic or quasi-azeotropic composition comprising 1,1,1,2,2-pentafluoropropane (245cb) and trans-1,3,3,3-tetrafluoro-1-propene (1234ze-E).

7. The process as claimed in claim 6, wherein said organic extracting agent has a separation factor $S_{1,2}$ of greater than or equal to 1.5, said separation factor being calculated by the formula $S_{1,2}=(\gamma_{1,S}*P1)/(\gamma_{2,S}*P2)$, wherein $\gamma_{1,S}$ represents the activity coefficient of 1,1,1,2,2-pentafluoropropane in said organic extracting agent at infinite dilution;

P1 represents the saturating vapor pressure of 1,1,1,2,2-pentafluoropropane;

$\gamma_{2,S}$ represents the activity coefficient of trans-1,3,3,3-tetrafluoro-1-propene in said organic extracting agent at infinite dilution; and P2 represents the saturating vapor pressure of trans-1,3,3,3-tetrafluoro-1-propene.

8. The process as claimed in claim 5, wherein said organic extracting agent has an absorption capacity $C_{2,S}$ of greater than or equal to 0.5, said absorption capacity being calculated by the formula $C_{2,S}=1/(\gamma_{2,S})$ wherein $\gamma_{2,S}$ represents the activity coefficient of trans-1,3,3,3-tetrafluoro-1-propene in said organic extracting agent at infinite dilution.

9. The process as claimed in claim 5, wherein said organic extracting agent is selected from the group consisting of ethylamine, isopropylamine, n-propylamine, diethylamine, propanone, 3-pentylamine, 2-methoxyethanamine, 2 pentanone, n-pentylamine, 1,2-diaminoethane, 1,2-propanediamine, and 1-ethoxy-2-propanol.

10. The process as claimed in claim 1, further comprising recovering said stream comprising 1,1,1,2,2-pentafluoropropane formed in step b) to be used in a process for producing 2,3,3,3-tetrafluoropropene.

11. A process for producing 2,3,3,3-tetrafluoro-1-propene, comprising:
A) fluorination in the presence of a catalyst for a compound of formula (I) $CX(Y)_2$—$CX(Y)_m$—$CH_mXY$ wherein X and Y independently represent a hydrogen, fluorine or chlorine atom and m=0 or 1 and/or fluorination in the presence of a catalyst for a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;
B) recovering a stream comprising 2,3,3,3-tetrafluoro-1-propene, 1,1,1,2,2-pentafluoropropane and at least one compound selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf);
C) distilling the stream recovered in step B) and recovering, at the top of the distillation column, a stream comprising 2,3,3,3-tetrafluoro-1-propene, and, at the bottom of the distillation column, a stream comprising 1,1,1,2,2-pentafluoropropane and at least one compound selected from the group consisting of 1,1-difluoroethane (152a), 1,1,1,2-tetrafluoroethane (134a), trans-1,3,3,3-tetrafluoro-1-propene (1234ze-E), cis-1,3,3,3-tetrafluoro-1-propene (1234ze-Z), trans-1,2,3,3,3-pentafluoropropene (1225ye-E), cis-1,2,3,3,3-pentafluoropropene (1225ye-Z) and 3,3,3-trifluoropropene (1243zf);
D) implementing the process for purifying 1,1,1,2,2-pentafluoropropane as claimed in claim 1 using the stream recovered at the bottom of the distillation column in step C); and
E) recycling into step A) the stream comprising 1,1,1,2,2-pentafluoropropane formed and recovered in step b) of the purification process performed in step D) or dehydrofluorinating the stream comprising 1,1,1,2,2-pentafluoropropane formed in step b) of the process for purifying 1,1,1,2,2-pentafluoropropane performed in step D) in the absence or presence of hydrofluoric acid.

* * * * *